(12) United States Patent
Srinivasan et al.

(10) Patent No.: US 8,877,512 B2
(45) Date of Patent: Nov. 4, 2014

(54) BUBBLE FORMATION TECHNIQUES USING PHYSICAL OR CHEMICAL FEATURES TO RETAIN A GAS BUBBLE WITHIN A DROPLET ACTUATOR

(75) Inventors: Vijay Srinivasan, Durham, NC (US); Michael G. Pollack, Durham, NC (US); Arjun Sudarsan, Cary, NC (US); Zhishan Hua, Durham, NC (US)

(73) Assignee: Advanced Liquid Logic, Inc., Research Triangle Park, NC (US)

( * ) Notice: Subject to any disclaimer, the term of this patent is extended or adjusted under 35 U.S.C. 154(b) by 647 days.

(21) Appl. No.: 12/692,954

(22) Filed: Jan. 25, 2010

(65) Prior Publication Data

US 2010/0190263 A1    Jul. 29, 2010

Related U.S. Application Data

(60) Provisional application No. 61/146,675, filed on Jan. 23, 2009.

(51) Int. Cl.
| | |
|---|---|
| G01N 1/10 | (2006.01) |
| B01L 3/00 | (2006.01) |
| B01F 13/00 | (2006.01) |
| C07K 1/26 | (2006.01) |
| G01N 1/22 | (2006.01) |
| G01N 35/10 | (2006.01) |

(52) U.S. Cl.
CPC .......... *C07K 1/26* (2013.01); *G01N 2001/2244* (2013.01); *B01L 3/502738* (2013.01); *B01L 2300/089* (2013.01); *B01L 2400/0427* (2013.01); *B01F 13/0076* (2013.01); *G01N 2035/1034* (2013.01); *B01F 13/0086* (2013.01); *B01L 2400/0406* (2013.01); *B01L 3/502792* (2013.01); *B01L 2300/0867* (2013.01); *B01F 13/0084* (2013.01); *B01L 2400/0688* (2013.01); *B01L 3/502723* (2013.01); *B01L 2200/0673* (2013.01)

USPC ....................................................... 436/174

(58) Field of Classification Search
USPC ....................................................... 436/174
See application file for complete search history.

(56) References Cited

U.S. PATENT DOCUMENTS

| 4,636,785 A | 1/1987 | Le Pesant |
| 5,181,016 A | 1/1993 | Lee et al. |

(Continued)

FOREIGN PATENT DOCUMENTS

| JP | 2006329899 A | 12/2006 |
| JP | 2006329904 A | 12/2006 |

(Continued)

OTHER PUBLICATIONS

Drucker, W. A. et al, Langmuir 1994, 10, 3279-3289.*

(Continued)

*Primary Examiner* — Arlen Soderquist
(74) *Attorney, Agent, or Firm* — William A. Barrett; Ward & Smith, P.A.

(57) ABSTRACT

The present invention is directed to a droplet actuator and methods of making and using the droplet actuator including one or more substrates configured to form a droplet operations gap and including a physical or chemical feature that may be provided at a predetermined locus within or exposed to the droplet operations gap and configured to retain a bubble in position within the droplet operations gap.

46 Claims, 16 Drawing Sheets

(56) References Cited

U.S. PATENT DOCUMENTS

| | | | |
|---|---|---|---|
| 5,486,337 A | 1/1996 | Ohkawa et al. | |
| 5,603,351 A * | 2/1997 | Cherukuri et al. | 506/33 |
| 5,879,632 A * | 3/1999 | Demers | 422/501 |
| 6,063,339 A | 5/2000 | Tisone et al. | |
| 6,130,098 A | 10/2000 | Handique et al. | |
| 6,294,063 B1 * | 9/2001 | Becker et al. | 204/450 |
| 6,565,727 B1 * | 5/2003 | Shenderov | 204/600 |
| 6,773,566 B2 | 8/2004 | Shenderov | |
| 6,790,011 B1 | 9/2004 | Le Pesant et al. | |
| 6,866,762 B2 * | 3/2005 | Gascoyne et al. | 204/547 |
| 6,893,547 B2 * | 5/2005 | Gascoyne et al. | 204/547 |
| 6,911,132 B2 * | 6/2005 | Pamula et al. | 204/600 |
| 6,924,792 B1 | 8/2005 | Jessop | |
| 6,977,033 B2 | 12/2005 | Becker et al. | |
| 6,989,234 B2 | 1/2006 | Kolar et al. | |
| 7,052,244 B2 | 5/2006 | Fouillet et al. | |
| 7,118,676 B2 * | 10/2006 | Mueth et al. | 210/732 |
| 7,163,612 B2 | 1/2007 | Sterling et al. | |
| 7,179,423 B2 * | 2/2007 | Bohm et al. | 422/504 |
| 7,211,223 B2 | 5/2007 | Fouillet et al. | |
| 7,255,780 B2 | 8/2007 | Shenderov | |
| 7,328,979 B2 | 2/2008 | Decre et al. | |
| 7,329,545 B2 | 2/2008 | Pamula et al. | |
| 7,439,014 B2 | 10/2008 | Pamula et al. | |
| 7,458,661 B2 | 12/2008 | Kim et al. | |
| 7,531,072 B2 | 5/2009 | Roux et al. | |
| 7,547,380 B2 | 6/2009 | Velev | |
| 7,569,129 B2 | 8/2009 | Pamula et al. | |
| 7,641,779 B2 | 1/2010 | Becker et al. | |
| 7,727,466 B2 | 6/2010 | Meathrel et al. | |
| 7,727,723 B2 | 6/2010 | Pollack et al. | |
| 7,759,132 B2 | 7/2010 | Pollack et al. | |
| 7,763,471 B2 | 7/2010 | Pamula et al. | |
| 7,815,871 B2 | 10/2010 | Pamula et al. | |
| 7,816,121 B2 | 10/2010 | Pollack et al. | |
| 7,822,510 B2 | 10/2010 | Paik et al. | |
| 7,851,184 B2 | 12/2010 | Pollack et al. | |
| 7,875,160 B2 | 1/2011 | Jary | |
| 7,901,947 B2 | 3/2011 | Pollack et al. | |
| 7,919,330 B2 | 4/2011 | De Guzman et al. | |
| 7,922,886 B2 | 4/2011 | Fouillet et al. | |
| 7,939,021 B2 | 5/2011 | Smith et al. | |
| 7,943,030 B2 | 5/2011 | Shenderov | |
| 7,989,056 B2 | 8/2011 | Plissonnier et al. | |
| 7,998,436 B2 | 8/2011 | Pollack | |
| 8,007,739 B2 | 8/2011 | Pollack et al. | |
| 8,041,463 B2 | 10/2011 | Pollack et al. | |
| 8,048,628 B2 | 11/2011 | Pollack et al. | |
| 8,075,754 B2 | 12/2011 | Sauter-Starace et al. | |
| 8,088,578 B2 | 1/2012 | Hua et al. | |
| 8,093,062 B2 | 1/2012 | Winger et al. | |
| 8,093,064 B2 | 1/2012 | Shah et al. | |
| 8,137,917 B2 | 3/2012 | Pollack et al. | |
| 8,147,668 B2 | 4/2012 | Pollack et al. | |
| 8,202,686 B2 | 6/2012 | Pamula et al. | |
| 8,208,146 B2 | 6/2012 | Srinivasan et al. | |
| 8,221,605 B2 | 7/2012 | Pollack et al. | |
| 8,236,156 B2 | 8/2012 | Sarrut et al. | |
| 8,268,246 B2 | 9/2012 | Srinivasan et al. | |
| 8,287,711 B2 | 10/2012 | Pollack et al. | |
| 8,304,253 B2 | 11/2012 | Yi et al. | |
| 8,313,698 B2 | 11/2012 | Pollack et al. | |
| 8,317,990 B2 | 11/2012 | Pamula et al. | |
| 8,342,207 B2 | 1/2013 | Raccurt et al. | |
| 8,349,276 B2 | 1/2013 | Pamula et al. | |
| 8,364,315 B2 | 1/2013 | Sturmer et al. | |
| 8,388,909 B2 | 3/2013 | Pollack et al. | |
| 8,389,297 B2 | 3/2013 | Pamula et al. | |
| 8,394,249 B2 | 3/2013 | Pollack et al. | |
| 8,426,213 B2 | 4/2013 | Eckhardt et al. | |
| 8,440,392 B2 | 5/2013 | Pamula et al. | |
| 8,444,836 B2 | 5/2013 | Fouillet et al. | |
| 2002/0005354 A1 | 1/2002 | Spence et al. | |
| 2002/0036139 A1 | 3/2002 | Becker et al. | |
| 2002/0043463 A1 | 4/2002 | Shenderov | |
| 2002/0058332 A1 | 5/2002 | Quake et al. | |
| 2002/0063060 A1 * | 5/2002 | Gascoyne et al. | 204/471 |
| 2002/0106314 A1 * | 8/2002 | Pelrine et al. | 422/186 |
| 2002/0143437 A1 | 10/2002 | Handique et al. | |
| 2002/0153092 A1 * | 10/2002 | Rinne | 156/278 |
| 2003/0087292 A1 * | 5/2003 | Chen et al. | 435/6 |
| 2003/0121788 A1 * | 7/2003 | Gascoyne et al. | 204/547 |
| 2003/0164295 A1 * | 9/2003 | Sterling | 204/450 |
| 2003/0173223 A1 * | 9/2003 | Gascoyne et al. | 204/547 |
| 2003/0183525 A1 * | 10/2003 | Elrod et al. | 204/547 |
| 2003/0196714 A1 * | 10/2003 | Gilbert et al. | 137/828 |
| 2003/0205632 A1 | 11/2003 | Kim et al. | |
| 2004/0031688 A1 * | 2/2004 | Shenderov | 204/600 |
| 2004/0055536 A1 * | 3/2004 | Kolar et al. | 118/626 |
| 2004/0055891 A1 * | 3/2004 | Pamula et al. | 205/98 |
| 2004/0058450 A1 * | 3/2004 | Pamula et al. | 436/150 |
| 2004/0091398 A1 * | 5/2004 | Gilbert et al. | 422/100 |
| 2004/0211659 A1 * | 10/2004 | Velev | 204/164 |
| 2004/0231987 A1 * | 11/2004 | Sterling et al. | 204/450 |
| 2006/0021875 A1 | 2/2006 | Griffith et al. | |
| 2006/0054503 A1 | 3/2006 | Pamula et al. | |
| 2006/0102477 A1 * | 5/2006 | Vann et al. | 204/450 |
| 2006/0114296 A1 * | 6/2006 | Gascoyne et al. | 347/73 |
| 2006/0164490 A1 | 7/2006 | Kim et al. | |
| 2006/0186048 A1 * | 8/2006 | Tan | 210/656 |
| 2006/0194331 A1 * | 8/2006 | Pamula et al. | 436/150 |
| 2006/0231398 A1 | 10/2006 | Sarrut et al. | |
| 2006/0254933 A1 * | 11/2006 | Adachi et al. | 205/777 |
| 2007/0023292 A1 | 2/2007 | Kim et al. | |
| 2007/0037294 A1 | 2/2007 | Pamula et al. | |
| 2007/0045117 A1 | 3/2007 | Pamula et al. | |
| 2007/0064990 A1 | 3/2007 | Roth | |
| 2007/0086927 A1 | 4/2007 | Natarajan et al. | |
| 2007/0099289 A1 * | 5/2007 | Irimia et al. | 435/287.2 |
| 2007/0207513 A1 | 9/2007 | Sorensen et al. | |
| 2007/0217956 A1 | 9/2007 | Pamula et al. | |
| 2007/0241068 A1 * | 10/2007 | Pamula et al. | 210/806 |
| 2007/0242105 A1 * | 10/2007 | Srinivasan et al. | 347/63 |
| 2007/0242111 A1 * | 10/2007 | Pamula et al. | 347/81 |
| 2007/0243634 A1 * | 10/2007 | Pamula et al. | 436/518 |
| 2007/0267294 A1 | 11/2007 | Shenderov | |
| 2007/0275415 A1 * | 11/2007 | Srinivasan et al. | 435/7.4 |
| 2008/0006535 A1 | 1/2008 | Paik et al. | |
| 2008/0018709 A1 * | 1/2008 | Takenaka et al. | 347/58 |
| 2008/0038810 A1 * | 2/2008 | Pollack et al. | 435/283.1 |
| 2008/0044893 A1 * | 2/2008 | Pollack et al. | 435/305.3 |
| 2008/0044914 A1 * | 2/2008 | Pamula et al. | 436/86 |
| 2008/0050834 A1 * | 2/2008 | Pamula et al. | 436/86 |
| 2008/0053205 A1 * | 3/2008 | Pollack et al. | 73/61.71 |
| 2008/0073216 A1 * | 3/2008 | Sugahara | 204/650 |
| 2008/0105549 A1 | 5/2008 | Pamela et al. | |
| 2008/0110753 A1 * | 5/2008 | Fourrier et al. | 204/403.01 |
| 2008/0124252 A1 | 5/2008 | Marchand et al. | |
| 2008/0142376 A1 | 6/2008 | Fouillet et al. | |
| 2008/0151240 A1 | 6/2008 | Roth | |
| 2008/0185296 A1 * | 8/2008 | Sauter-Starace et al. | 205/777.5 |
| 2008/0210558 A1 | 9/2008 | Sauter-Starace et al. | |
| 2008/0230386 A1 * | 9/2008 | Srinivasan et al. | 204/450 |
| 2008/0247920 A1 | 10/2008 | Pollack et al. | |
| 2008/0264797 A1 | 10/2008 | Pamula et al. | |
| 2008/0274513 A1 | 11/2008 | Shenderov et al. | |
| 2008/0277615 A1 * | 11/2008 | Gilbert et al. | 251/335.1 |
| 2008/0281471 A1 | 11/2008 | Smith et al. | |
| 2008/0283414 A1 | 11/2008 | Monroe et al. | |
| 2008/0302431 A1 | 12/2008 | Marchand et al. | |
| 2008/0305481 A1 | 12/2008 | Whitman et al. | |
| 2009/0014394 A1 | 1/2009 | Yi et al. | |
| 2009/0042319 A1 | 2/2009 | De Guzman et al. | |
| 2009/0127123 A1 | 5/2009 | Raccurt et al. | |
| 2009/0134027 A1 | 5/2009 | Jary | |
| 2009/0142564 A1 | 6/2009 | Plissonnier et al. | |
| 2009/0155902 A1 | 6/2009 | Pollack et al. | |
| 2009/0192044 A1 | 7/2009 | Fouillet | |
| 2009/0260988 A1 | 10/2009 | Pamula et al. | |
| 2009/0263834 A1 | 10/2009 | Sista et al. | |
| 2009/0280251 A1 | 11/2009 | De Guzman et al. | |
| 2009/0280475 A1 * | 11/2009 | Pollack et al. | 435/6 |
| 2009/0280476 A1 * | 11/2009 | Srinivasan et al. | 435/6 |
| 2009/0283407 A1 | 11/2009 | Shah et al. | |

(56) References Cited

U.S. PATENT DOCUMENTS

| | | |
|---|---|---|
| 2009/0288710 A1 | 11/2009 | Viovy et al. |
| 2009/0291433 A1* | 11/2009 | Pollack et al. .................... 435/6 |
| 2009/0304944 A1 | 12/2009 | Sudarsan et al. |
| 2009/0311713 A1 | 12/2009 | Pollack et al. |
| 2009/0321262 A1 | 12/2009 | Adachi et al. |
| 2010/0025242 A1 | 2/2010 | Pamula et al. |
| 2010/0025250 A1 | 2/2010 | Pamula et al. |
| 2010/0027100 A1* | 2/2010 | Lee et al. ...................... 359/290 |
| 2010/0028920 A1 | 2/2010 | Eckhardt |
| 2010/0032293 A1 | 2/2010 | Pollack et al. |
| 2010/0041046 A1* | 2/2010 | Chiu et al. ........................ 435/6 |
| 2010/0041086 A1 | 2/2010 | Pamula et al. |
| 2010/0048410 A1 | 2/2010 | Shenderov et al. |
| 2010/0062508 A1 | 3/2010 | Pamula et al. |
| 2010/0068764 A1 | 3/2010 | Sista et al. |
| 2010/0087012 A1 | 4/2010 | Shenderov et al. |
| 2010/0096266 A1 | 4/2010 | Kim |
| 2010/0116640 A1 | 5/2010 | Pamula et al. |
| 2010/0118307 A1* | 5/2010 | Srinivasan et al. ............. 356/436 |
| 2010/0120130 A1* | 5/2010 | Srinivasan et al. ......... 435/283.1 |
| 2010/0126860 A1 | 5/2010 | Srinivasan et al. |
| 2010/0130369 A1 | 5/2010 | Shenderov et al. |
| 2010/0140093 A1 | 6/2010 | Pamula et al. |
| 2010/0143963 A1 | 6/2010 | Pollack |
| 2010/0151439 A1 | 6/2010 | Pamula et al. |
| 2010/0190263 A1 | 7/2010 | Srinivasan et al. |
| 2010/0194408 A1 | 8/2010 | Sturmer et al. |
| 2010/0221713 A1 | 9/2010 | Pollack et al. |
| 2010/0236927 A1 | 9/2010 | Pope et al. |
| 2010/0236928 A1 | 9/2010 | Srinivasan et al. |
| 2010/0236929 A1 | 9/2010 | Pollack et al. |
| 2010/0258441 A1 | 10/2010 | Sista et al. |
| 2010/0270156 A1* | 10/2010 | Srinivasan et al. ............ 204/450 |
| 2010/0279374 A1 | 11/2010 | Sista et al. |
| 2010/0282608 A1 | 11/2010 | Srinivasan et al. |
| 2010/0282609 A1 | 11/2010 | Pollack et al. |
| 2010/0307917 A1 | 12/2010 | Srinivasan et al. |
| 2010/0320088 A1 | 12/2010 | Fouillet et al. |
| 2010/0323405 A1 | 12/2010 | Pollack et al. |
| 2011/0086377 A1 | 4/2011 | Thwar et al. |
| 2011/0091989 A1 | 4/2011 | Sista et al. |
| 2011/0097763 A1 | 4/2011 | Pollack et al. |
| 2011/0100823 A1 | 5/2011 | Pollack et al. |
| 2011/0104725 A1 | 5/2011 | Pamula et al. |
| 2011/0104747 A1 | 5/2011 | Pollack et al. |
| 2011/0104816 A1 | 5/2011 | Pollack et al. |
| 2011/0114490 A1 | 5/2011 | Pamula et al. |
| 2011/0118132 A1 | 5/2011 | Winger et al. |
| 2011/0180571 A1 | 7/2011 | Srinivasan et al. |
| 2011/0186433 A1 | 8/2011 | Pollack et al. |
| 2011/0203930 A1 | 8/2011 | Pamula et al. |
| 2011/0209998 A1 | 9/2011 | Shenderov |
| 2011/0213499 A1 | 9/2011 | Sturmer et al. |
| 2011/0303542 A1 | 12/2011 | Srinivasan et al. |
| 2011/0311980 A1 | 12/2011 | Pollack et al. |
| 2012/0018306 A1 | 1/2012 | Srinivasan et al. |
| 2012/0132528 A1 | 5/2012 | Shenderov et al. |
| 2012/0165238 A1 | 6/2012 | Pamula et al. |

FOREIGN PATENT DOCUMENTS

| | | |
|---|---|---|
| WO | 0069565 A1 | 11/2000 |
| WO | 0073655 A1 | 12/2000 |
| WO | 2004029585 A1 | 4/2004 |
| WO | 2004030820 | 4/2004 |
| WO | 2005047696 A1 | 5/2005 |
| WO | 2006013303 A1 | 2/2006 |
| WO | 2006070162 A1 | 7/2006 |
| WO | 2006081558 | 8/2006 |
| WO | 2006124458 A2 | 11/2006 |
| WO | 2006127451 A2 | 11/2006 |
| WO | 2006134307 A1 | 12/2006 |
| WO | 2006138543 | 12/2006 |
| WO | 2007003720 A1 | 1/2007 |
| WO | 2007012638 A1 | 2/2007 |
| WO | 2007033990 A1 | 3/2007 |
| WO | 2007048111 | 4/2007 |
| WO | 2007120240 A2 | 10/2007 |
| WO | 2007120241 A2 | 10/2007 |
| WO | 2007123908 A2 | 11/2007 |
| WO | 2008051310 A2 | 5/2008 |
| WO | 2008055256 A3 | 5/2008 |
| WO | 2008068229 A1 | 6/2008 |
| WO | 2008091848 A2 | 7/2008 |
| WO | 2008098236 A2 | 8/2008 |
| WO | 2008101194 A2 | 8/2008 |
| WO | 2008106678 A1 | 9/2008 |
| WO | 2008109664 A1 | 9/2008 |
| WO | 2008112856 A1 | 9/2008 |
| WO | 2008116209 A1 | 9/2008 |
| WO | 2008116221 A1 | 9/2008 |
| WO | 2008118831 A2 | 10/2008 |
| WO | 2008124846 A2 | 10/2008 |
| WO | 2008131420 A2 | 10/2008 |
| WO | 2008134153 A1 | 11/2008 |
| WO | 2009002920 A1 | 12/2008 |
| WO | 2009003184 A1 | 12/2008 |
| WO | 2009011952 A1 | 1/2009 |
| WO | 2009021173 A1 | 2/2009 |
| WO | 2009021233 A2 | 2/2009 |
| WO | 2009026339 A2 | 2/2009 |
| WO | 2009029561 A2 | 3/2009 |
| WO | 2009032863 A2 | 3/2009 |
| WO | 2009052095 A1 | 4/2009 |
| WO | 2009052123 A2 | 4/2009 |
| WO | 2009052321 A2 | 4/2009 |
| WO | 2009052345 | 4/2009 |
| WO | 2009052348 A2 | 4/2009 |
| WO | 2009076414 | 6/2009 |
| WO | 2009086403 A2 | 7/2009 |
| WO | 2009111769 A2 | 9/2009 |
| WO | 2009135205 A2 | 11/2009 |
| WO | 2009137415 A2 | 11/2009 |
| WO | 2009140373 A2 | 11/2009 |
| WO | 2009140671 A2 | 11/2009 |
| WO | 2010006166 A2 | 1/2010 |
| WO | 2010009463 A2 | 1/2010 |
| WO | 2010019782 A2 | 2/2010 |
| WO | 2010027894 A2 | 3/2010 |
| WO | 2010042637 A2 | 4/2010 |
| WO | 2010077859 A3 | 7/2010 |

OTHER PUBLICATIONS

Attard, P., Langmuir 2000, 16, 4455-4466.*
Taniguchi, T. et al, Lab on a Chip 2002, 2, 19-21.*
Lee, J. et al, Sensors and Actuators A 2002, 95, 259-268.*
Tseng, F.-G. et al, Journal of Microelectromechanical Systems 2002, 11, 427-436.*
Ito, T. et al, 2003 IEEE The Sixteenth Annual International Conference on Micro Electro Mechanical Systems, MEMS-03 Kyoto, 335-338.*
Jones, T. B. et al, Langmuir 2003, 19, 7646-7651.*
Schwartz, J. A. et al, Lab on a Chip 2004, 4, 11-17.*
Srinivasan, V. et al, Analytica Chimica Acta 2004, 507, 145-150.*
Satoh, W. et al, Journal of Applied Physics 2004, 96, 835-841.*
Zhao, Y. et al, 2005 IEEE International Conference on Robotics and Biomimetics (ROBIO), 269-273.*
Quere, D., Reports on Progress in Physics 2005, 68, 2495-2532.*
Satoh, W. et al, Analytical Chemistry 2005, 77, 6857-6863.*
Ahmed, R. et al, Journal of Electrostatics 2006, 64, 543-549.*
Zhao, Y. et al, Lab on a Chip 2007, 7, 273-280.*
Hirvi, J. T. et al, Journal of Physical Chemistry B 2007, 111, 3336-3341.*
Boyd, D. A. et al, Analytical Chemistry 2008, 80, 2452-2456.*
Sista, R. et al, Lab on a Chip 2008, 8, 2091-2104.*
Chatterjee, Debalina. "Lab on a Chip Applications with a Digital Microfluidic Platform," UCLA Dissertation 2008, UMI Microform No. 3342975, document size 186 pages.

(56) References Cited

OTHER PUBLICATIONS

Fair, et al., "Integrated chemical/biochemical sample collection, preconcentration, and analysis on a digital microfluidic lab-on-a-chip platform," Lab-on-a-Chip: Platforms, Devices, and Applications, Conf. 5591, SPIE Optics East, Philadelphia, Oct. 25-28, 2004.

Terry, S.C., J.H. Jerman, and J.B. Angell, "A Gas Chromatographic Air Analyzer Fabricated on a Silicon Wafer," IEEE Transactions on Electron Devices, vol. ED-26, 1979, pp. 1880-1886.

Tuckerman, D.B. and R.F.W. Pease, "High-Performance Heat Sinking for VLSI," IEEE Electron Device Letters, 1981, pp. 126-129.

Batchelder, J.S., "Dielectrophoretic manipulator," Review of Scientific Instruments, vol. 54, 1983, pp. 300-302.

Manz, A., N. Graber, and H.M. Widmer, "Miniaturized Total Chemical Analysis Systems: a Novel Concept for Chemical Sensing," Sensors and Actuators B: Chemical, 1990, pp. 244-248.

Welters, W.J.J. and L.G.J. Fokkink, "Fast Electrically Switchable Capillary Effects," Langmuir, vol. 14, Mar. 1998, pp. 1535-1538.

McDonald, J.C., D.C. Duffy, J.R. Anderson, D.T. Chiu, H. Wu, O.J.A. Schuueller, and G.M. Whitesides, "Fabrication of Microfluidic systems in poly (dimethylsiloxane)," Electrophoresis, vol. 21, 2000, pp. 27-40.

A. Wego, S. Richter, L. Pagel, "Fluidic microsystems based on printed circuit board technology," Journal of Micromechanics and Microengineering, vol. 11, No. 5, pp. 528-531 (Sep. 2001).

Moon H, Cho SK, Garrell RL, et al., "Low voltage electrowetting-on-dielectric," Journal of Applied Physics, vol. 92 (7): pp. 4080-4087, Oct. 1, 2002.

Becker, H., et al. "Polymer microfluidic devices," Talanta, vol. 56, Feb. 2002, pp. 267-287.

Yoon, J.-Y. et al., "Preventing Biomolecular Adsorption in Electrowetting-Based Biofluidic Chips," Analytical Chemistry, vol. 75, Oct. 2003, pp. 5097-5102.

P.Y. Chiou, H. Moon, H. Toshiyoshi, C.-J. Kim, and M.C. Wu, "Light actuation of liquid by optoelectrowetting," Sensors and Actuators A: Physical, vol. 104, May 2003, pp. 222-228.

Squires, T.M. and S.R. Quake, "Microfluidics: Fluid physics at the nanoliter scale," Reviews of Modern Physics, vol. 77, Oct. 2005, pp. 977-1026.

Fouillet, Y., D. Jary, A.G. Brachet, C. Chabrol, J. Boutet, P. Clementz, R. Charles, and C. Peponnet, "Design and Validation of a Complex Generic Fluidic Microprocessor Based on EWOD Droplet for Biological Applications," 9th International Conference on Miniaturized Systems for Chemistry and Life Sciences (MicroTAS), Boston, MA: 2005, pp. 58-60.

Z. Guttenberg, H. Muller, H. Habermuller, A. Geisbauer, J. Pipper, J. Felbel, M. Kielpinski, J. Scriba, and A. Wixforth, "Planar chip devices for PCR and hybridization with surface acoustic wave pump.," Lab on a chip, vol. 5, Mar. 2005, pp. 12617-12622.

Yager, P., T. Edwards, E. Fu, K. Helton, K. Nelson, M.R. Tam, and B.H. Weigl, "Microfluidic diagnostic technologies for global public health," Nature, vol. 442, 2006, pp. 412-418.

Cooney, C.G., C-Y. Chen, M.R. Emerling, A Nadim, and J.D. Sterling, Microfluidics and Nanofluidics, vol. 2 Mar. 2006, pp. 435-446.

Chatterjee, D., B. Hetayothin, A.R. Wheeler, D.J. King, and R.L. Garrell, "Droplet-based microfluidics with nonaqueous solvents and solutions.," Lab on a Chip, vol. 6, Feb. 2006, pp. 199-206.

M.Madou, J. Zoval, G. Jia, H. Kido, J. Kim, "Lab on a CD," Annual Review of Biomedical Engineering, vol. 8, pp. 601-628, 2006.

Yi, U.-C. and C.-J. Kim, "Characterization of electrowetting actuation on addressable single-side coplanar electrodes," Journal of Micromechanics and Microengineering, vol. 16, Oct. 2006, pp. 2053-2059.

Dubois, P., G. Marchand, Y. Fouillet, J. Berthier, T. Douki, F. Hassine, S. Gmouh, and M. Vaultier, "Ionic Liquid Droplet as e-Microreactor," Analytical Chemistry, vol. 78, 2006, pp. 4909-4917.

Whitesides, G.M., "The origins and the future of microfluidics," Nature, vol. 442, 2006, pp. 368-373.

Chin, C.D., V. Linder, and S.K. Sia, "Lab-on-a-chip devices for global health: past studies and future opportunities.," Lab on a Chip, vol. 7, Jan. 2007, pp. 41-57.

Baviere, R., J. Boutet, and Y. Fouillet, "Dynamics of droplet transport induced by electrowetting actuation," Microfluidics and Nanofluidics, vol. 4, May 2007, pp. 287-294.

Paik, P.Y., V.K. Pamula, and K. Chakrabarty, "A Digital-Microfluidic Approach to Chip Cooling," IEEE Design & Test of Computers, vol. 25, Jul. 2008, pp. 372-381.

Teh, S.-Y., R. Lin, L.-H. Hung, and A.P. Lee, "Droplet microfluidics.," Lab on a chip, vol. 8 Feb. 2008, pp. 198-220.

Huebner, A., S. Sharma, M. Srisa-Art, F. Hollfelder, J.B. Edel, and A.J. DeMello, "Microdroplets: a sea of applications?," Lab on a Chip, vol. 8, Aug. 2008, pp. 1244-1254.

Gong, J. and C.-J.C. Kim, "Direct-referencing two-dimensional-array digital microfluidics using multi-layer printed circuit board," Journal of Microelectromechanical Systems, vol. 17, Jan. 2008, pp. 257-264.

Miller, E.M. and A.R. Wheeler, "A Digital Microfluidic Approach to Homogeneous Enzyme Assays," Analytical Chemistry, vol. 80, 2008, pp. 1614-1619.

R.S. Sista, A.E. Eckhardt, V. Srinivasan, M.G. Pollack, S. Palanki, and V.K. Pamula, "Heterogeneous immunoassays using magnetic beads on a digital microfluidic platform," Lab on a Chip, vol. 8, Dec. 2008, pp. 2188-2196.

Luk, V.N.,Pluronic additives: a solution to sticky problems in digital microfluidics.,: Langmuir: the ACS journal of surfaces ans colloids, vol. 24, Jun. 2008, pp. 6382-6389.

L. Luan, R.D. Evans, N.M. Jokerst, and R.B. Fair, "Integrated Optical Sensor in a Digital Microfluidic Platform," IEEE Sensors Journal, vol. 8, May 2008, pp. 628-635.

R. Mariella, "Sample preparation: the weak link in microfluidics-based biodetection.," Biomedical Microdevices, vol. 10, Dec. 2008, pp. 777-784.

D. Brassard, L. Malic, F. Normandin, M. Tabrizian, and T. Veres, "Water-oil core-shell droplets for electrowetting-based digital microfluidic devices.," Lab on a chip, vol. 8, Aug. 2008, pp. 1342-1349.

R. Mukhopadhyay, "Microfluidics: on the slope of enlightenment.," Analytical chemsitry vol. 81, Jun. 2009, pp. 4169-4173.

N.A. Mousa, M.J. Jebrail, H.Yang, M. Abdelgawad, P. Metalnikov, J. Chen, A.R. Wheeler, and R.F. Casper, "Droplet-scale estrogen assays in breast tissue, blood, and serum.," Science Translational Medicine, vol. 1 Oct. 2009, p. Ira2.

J.L. Poulos, W.C. Nelson, T.-J. Jeon, C.-J. "CJ" Kim, and J.J. Schmidt, "Electrowetting on dielectric-based microfluidics for integrated lipid bilayer formation and measurement," Applied Physics Letters, vol. 95, 2009, p. 013706.

S.M. Langelier, D.S. Chang, R.I. Zeitoun, and M. a Burns, "Acoustically driven programmable liquid motion using resonance cavities" Proceedings of the National Academy of Sciences of the USA, vol. 106, Aug. 2009, pp. 12617-12622.

L. Malic, T. Veres, and M. Tabrizian, "Biochip functionalization using electrowetting-on-dielectric digital microfluidics for surface plasmon resonance imaging detection of DNA hybridization.," Biosensors & Bioelectronics, vol. 24, Mar. 2009, pp. 2218-2224.

G.J. Shah, A.T. Ohta, E.P.-Y. Chiou, M.C. Wu, and C.-J.C.J. Kim, "EWOD-driven droplet microfluidic device integrated with optoelectronic tweezers as an automated platform for cellular isolation and analysis.," Lab on a Chip, vol. 9, Jun. 2009, pp. 1732-1739.

Chakrabarty, "Automated Design of Microfluidics-Based Biochips: connecting Biochemistry of Electronics CAD", IEEE International Conference on Computer Design, San Jose, CA, Oct. 1-4, 2006, 93-100.

Chakrabarty et al., "Design Automation Challenges for Microfluidics-Based Biochips", DTIP of MEMS & MOEMS, Montreux, Switzerland, Jun. 1-3, 2005, 6 pages.

Chakrabarty et al., "Design Automation for Microfluidics-Based Biochips", ACM Journal on Engineering Technologies in Computing Systems, 1(3), Oct. 2005, 186-223.

Chakrabarty, "Design, Testing, and Applications of Digital Microfluidics-Based Biochips", Proceedings of the 18th International Conf. on VLSI held jointly with 4th International Conf. on Embedded Systems Design (VLSID'05), IEEE, Jan. 3-7, 2005, 6 pages.

(56) References Cited

OTHER PUBLICATIONS

Chen et al., "Development of Mesoscale Actuator Device with Micro Interlocking Mechanism", J. Intelligent Material Systems and Structures, vol. 9, No. 4, Jun. 1998, pp. 449-457.
Chen et al., "Mesoscale Actuator Device with Micro Interlocking Mechanism", Proc. IEEE Micro Electro Mechanical Systems Workshop, Heidelberg, Germany, Jan. 1998, pp. 384-389.
Chen et al., "Mesoscale Actuator Device: Micro Interlocking Mechanism to Transfer Macro Load", Sensors and Actuators, vol. 73, Issues 1-2, Mar. 1999, pp. 30-36.
Cotten et al., "Digital Microfluidics: a novel platform for multiplexed detection of lysosomal storage diseases", Abstract #3747.9. Pediatric Academic Society Conference, 2008, 1 page.
Delattre et al., "Towards an industrial fabrication process for electrowetting chip using standard MEMS Technology", μTAS2008, San Diego; poster presented, Oct. 15, 2008.
Delattre et al., "Towards an industrial fabrication process for electrowetting chip using standard MEMS Technology", μTAS2008, San Diego; Abstract in proceedings, Oct. 13-16, 2008, 1696-1698.
Dewey, "Towards a Visual Modeling Approach to Designing Microelectromechanical System Transducers", Journal of Micromechanics and Microengineering, vol. 9, Dec. 1999, 332-340.
Dewey et al., "Visual modeling and design of microelectromechanical system tansducers", Microelectronics Journal, vol. 32, Apr. 2001, 373-381.
Fair et al., "A Micro- Watt Metal-Insulator-Solution-Transport (MIST) Device for Scalable Digital Bio-Microfluidic Systems", IEEE IEDM Technical Digest, 2001, 16.4.1-4.
Fair et al., "Advances in droplet-based bio lab-on-a-chip", BioChips 2003, Boston, 2003, 24 pages.
Fair et al., "Bead-Based and Solution-Based Assays Performed on a Digital Microfluidic Platform", Biomedical Engineering Society (BMES) Fall Meeting, Baltimore, MD, Oct. 1, 2005, 31 pages.
Fair, "Biomedical Applications of Electrowetting Systems", 5th International Electrowetting Workshop, Rochester, NY, May 31, 2006, abstract.
Fair et al., "Chemical and Biological Applications of Digital-Microfluidic Devices", IEEE Design & Test of Computers, vol. 24(1), Jan.-Feb. 2007, 10-24.
Fair et al., "Chemical and biological pathogen detection in a digital microfluidic platform", DARPA Workshop on Microfluidic Analyzers for DoD and National Security Applications, Keystone, CO, 2006, abstract.
Fair, "Digital microfluidics: is a true lab-on-a-chip possible?", Microfluid Nanofluid, vol. 3, Mar. 8, 2007, 245-281.
Fair, "Droplet-based microfluidic Genome sequencing", NHGRI PI's meeting, Boston, 2005, 12 pages.
Fair et al., "Electrowetting-based On-Chip Sample Processing for Integrated Microfluidics", IEEE Inter. Electron Devices Meeting (IEDM), 2003, 32.5.1-32.5.4.
Fair, "Scaling of Digital Microfluidic Devices for Picoliter Applications", The 6th International Electrowetting Meeting, Aug. 20-22, 2008, p. 14.
Fouillet, "Bio-Protocol Integration in Digital Microfluidic Chips", The 6th International Electrowetting Meeting, Aug. 20-22, 2008, p. 15.
Fouillet et al., "Digital microfluidic design and optimization of classic and new fluidic functions for lab on a chip systems", Microfluid Nanofluid, vol. 4, 2008, 159-165.
Hua et al., "Rapid Detection of Methicillin-Resistant *Staphylococcus aureus* (MRSA) Using Digital Microfluidics", 12th Intl Conference on Miniaturized Systems for Chemistry and Life Sciences, Proc. μTAS, Oct. 12-16, 2008, 1713-1715.
Jun et al., "Valveless Pumping using Traversing Vapor Bubbles in Microchannels", J. Applied Physics, vol. 83, No. 11, Jun. 1998, pp. 5658-5664.
Kim et al., "MEMS Devices Based on the Use of Surface Tension", Proc. Int. Semiconductor Device Research Symposium (ISDRS'99), Charlottesville, VA, Dec. 1999, pp. 481-484.

Kim, "Microelectromechanical Systems (MEMS) at the UCLA Micromanufacturing Lab", Dig. Papers, Int. Microprocesses and Nanotechnology Conf. (MNC'98), Kyungju, Korea, Jul. 1998, pp. 54-55.
Kim et al., "Micromachines Driven by Surface Tension", AIAA 99-3800, 30th AIAA Fluid Dynamics Conference, Norfolk, VA, (Invited lecture), Jun. 1999, pp. 1-6.
Kleinert et al., "Electric Field-Assisted Convective Assembly of Large-Domain Colloidal Crystals", The 82nd Colloid & Surface Science Symposium, ACS Division of Colloid & Surface Science, North Carolina State University, Raleigh, NC. www.colloids2008.org., Jun. 15-18, 2008, 134-135.
Lee et al., "Microactuation by Continuous Electrowetting Phenomenon and Silicon Deep Rie Process", Proc. MEMS (DSC—vol. 66) ASME Int. Mechanical Engineering Congress and Exposition, Anaheim, CA, Nov. 1998, 475-480.
Lee et al., "Liquid Micromotor Driven by Continuous Electrowetting", Proc. IEEE Micro Electro Mechanical Systems Workshop, Heidelberg, Germany, Jan. 1998, pp. 538-543.
Lee et al., "Theory and Modeling of Continuous Electrowetting Microactuation", Proc. MEMS (MEMS-vol. 1), ASME Int. Mechanical Engineering Congress and Exposition, Nashville, TN, Nov. 1999, pp. 397-403.
Marchand et al., "Organic Synthesis in Soft Wall-Free Microreactors: Real-Time Monitoring of Fluorogenic Reactions", Analytical Chemistry, vol. 80, Jul. 2, 2008, 6051-6055.
Millington et al., "Digital Microfluidics: a novel platform for multiplexed detection of LSDs with potential for newborn screening", Association of Public Health Laboratories Annual Conference, San Antonio, TX, Nov. 4, 2008, 26 pages.
Millington et al., "Digital Microfluidics: A Novel Platform for Multiplexing Assays Used In Newborn Screening", Proceedings of the 7th International and Latin American Congress. Oral Presentations. Rev Invest Clin; vol. 61 (Supl. 1), 2009, 241-33.
Paik et al., "Adaptive Cooling of Integrated Circuits Using Digital Microfluidics", IEEE Transactions on VLSI, vol. 16, No. 4, 2008, 432-443.
Paik et al., "Adaptive Cooling of Integrated Circuits Using Digital Microfluidics", accepted for publication in IEEE Transactions on VLSI Systems, 2007, and Artech House, Norwood, MA, 2007, 192 pages.
Paik, "Adaptive Hot-Spot Cooling of Integrated Circuits Using Digital Microfluidics", Dissertation, Dept. Of Electrical and Computer Engineering, Duke University, Apr. 25, 2006, 1-188.
Paik et al., "Adaptive hot-spot cooling of integrated circuits using digital microfluidics", Proceedings ASME International Mechanical Engineering Congress and Exposition, Orlando, Florida, USA., Nov. 5-11, 2005, 1-6.
Paik et al., "Coplanar Digital Microfluidics Using Standard Printed Circuit Board Processes", 9th International Conference on Miniaturized Systems for Chemistry and Life Sciences (MicroTAS), Boston, MA; Poster, 2005, 1 page.
Paik et al., "Coplanar Digital Microfluidics Using Standard Printed Circuit Board Processes", 9th Int'l Conf. on Miniaturized Systems for Chemistry and Life Sciences, Boston, MA, Oct. 9-13, 2005, 566-68.
Paik et al., "Droplet-Based Hot Spot Cooling Using Topless Digital Microfluidics on a Printed Circuit Board", Int'l Workshops on Thermal Investigations of ICs and Systems (THERMINIC), 2005, 278-83.
Paik et al., "Electrowetting-based droplet mixers for microfluidic systems", Lab on a Chip (LOC), vol. 3. (more mixing videos available, along with the article, at LOC's website), 2003, 28-33.
Paik et al., "Programmable Flow-Through Real Time PCR Using Digital Microfluidics", 11th International Conference on Miniaturized Systems for Chemistry and Life Sciences, Paris, France, Oct. 7-11, 2007, 1559-1561.
Paik et al., "Programmable flow-through real-time PCR using digital microfluidics", Proc. Micro Total Analysis Systems (μTAS), Handout, 2007, 2 pages.
Paik et al., "Programmable flow-through real-time Pcr using digital microfluidics", Proc. Micro Total Analysis Systems (μTAS), Poster, 2007, 1 page.

(56) References Cited

OTHER PUBLICATIONS

Paik et al., "Rapid Droplet Mixers for Digital Microfluidic Systems", Masters Thesis, Duke Graduate School., 2002, 1-82.
Paik et al., "Rapid droplet mixers for digital microfluidic systems", Lab on a Chip, vol. 3. (More mixing videos available, along with the article, at LOC's website.), 2003, 253-259.
Paik et al., "Thermal effects on Droplet Transport in Digital Microfluids with Application to Chip Cooling Processing for Integrated Microfluidics", International Conference on Thermal, Mechanics, and Thermomechanical Phenomena in Electronic Systems (ITherm), 2004, 649-654.
Pamula, "A digital microfluidic platform for multiplexed explosive detection", Chapter 18, Electronics Noses and Sensors for the Detection of Explosives, Eds., J.W. Gardner and J. Yinon, Kluwer Academic Publishers, 2004, 279-288.
Pamula et al., "A droplet-based lab-on-a-chip for colorimetric detection of nitroaromatic explosives", Proceedings of Micro Electro Mechanical Systems, 2005, 722-725.
Pamula et al., "Cooling of integrated circuits using droplet-based microfluidics", Proc. ACM Great Lakes Symposium on VLSI, Apr. 2003, 84-87.
Pamula et al., "Digital microfluidic lab-on-a-chip for protein crystallization", 5th Protein Structure Initiative "Bottlenecks" Workshop, NIH, Bethesda, MD, Apr. 13-14, 2006, I-16.
Pamula et al., "Digital Microfluidics Platform for Lab-on-a-chip applications", Duke University Annual Post Doctoral Research Day, 2002, 1 page.
Pamula et al., "Microfluidic electrowetting-based droplet mixing", IEEE, 2002, 8-10.
Pollack, et al., "Electrowetting-Based Actuation of Droplets for Integrated Microfluidics", Lab on a Chip (LOC), vol. 2, 2002, 96-101.
Pollack et al., "Electrowetting-based actuation of liquid droplets for microfluidic applications", Appl. Phys. Letters, vol. 77, No. 11, Sep. 11, 2000, 1725-1726.
Pollack, "Electrowetting-based Microactuation of Droplets for Digital Microfluidics", PhD Thesis, Department of Electrical and Computer Engineering, Duke University, 2001, 159 pages.
Pollack et al., "Electrowetting-Based Microfluidics for High-Throughput Screening", smallTalk 2001 Conference Program Abstract, San Diego, Aug. 27-31, 2001, 149.
Pollack et al., "Investigation of electrowetting-based microfluidics for real-time PCR applications", Proc. 7th Int'l Conference on Micro Total Analysis Systems (mTAS), Squaw Valley, CA, Oct. 5-9, 2003, 619-622.
Pollack, "Lab-on-a-chip platform based digital microfluidics", The 6th International Electrowetting Meeting, Aug. 20-22, 2008, 16.
Ren et al., "Automated electrowetting-based droplet dispensing with good reproducibility", Proc. Micro Total Analysis Systems (mTAS), 7th Int. Conf. on Miniaturized Chem and Biochem Analysis Systems, Squaw Valley, CA, Oct. 5-9, 2003, 993-996.
Ren et al., "Automated on-chip droplet dispensing with vol. control by electro-wetting actuation and capacitance metering", Sensors and Actuators B: Chemical, vol. 98, Mar. 2004, 319-327.
Ren et al., "Design and testing of an interpolating mixing architecture for electrowettingbased droplet-on-chip chemical dilution", Transducers, 12th International Conference on Solid-State Sensors, Actuators and Microsystems, 2003, 619-622.
Ren et al., "Dynamics of electro-wetting droplet transport", Sensors and Actuators B (Chemical), vol. B87, No. 1, Nov. 15, 2002, 201-206.
Ren et al., "Micro/Nano Liter Droplet Formation and Dispensing by Capacitance Metering and Electrowetting Actuation", IEEE-NANO, 2002, 369-372.
Rival et al., "Towards Single Cells Gene Expression on EWOD Lab on Chip", ESONN 2008, Grenoble, France; Poster presented, Aug. 26, 2008.
Rival et al., "Towards single cells gene expression on EWOD lab on chip", ESONN, Grenoble, France, abstract in proceedings, Aug. 2008.
Rouse et al., "Digital microfluidics: a novel platform for multiplexing assays used in newborn screening", Poster 47, 41st AACC's Annual Oak Ridge Conference Abstracts, Clinical Chemistry, vol. 55, 2009, 16.
Sherman et al., "Flow Control by Using High-Aspect-Ratio, In-Plane Microactuators", Sensors and Actuators, vol. 73, 1999, pp. 169-175.
Sherman et al., "In-Plane Microactuator for Fluid Control Application", Proc. IEEE Micro Electro Mechanical Systems Workshop, Heidelberg, Germany, Jan. 1998, pp. 454-459.
Sista et al., "96-Immunoassay Digital Microfluidic Multiwell Plate", Proc. μTAS, Oct. 12-16, 2008, 447-449.
Sista, "Development of a Digital Microfluidic Lab-on-a-Chip for Automated Immunoassays with Magnetically Responsive Beads", PhD Thesis, Department of Chemical Engineering, Florida State University, 2007, 127 pages.
Sista et al., "Spatial multiplexing of immunoassays for small-vol. samples", 10th PI Meeting IMAT, Bethesda, 2009, 51-52.
Srinivasan et al., "3-D imaging of moving droplets for microfluidics using optical coherence tomography", Proc. 7th International Conference on Micro Total Analysis Systems (mTAS), Squaw Valley, CA, Oct. 5-9, 2003, 1303-1306.
Srinivasan et al., "A digital microfluidic biosensor for multianalyte detection", Proc. IEEE 16th Annual Int'l Conf. on Micro Electro Mechanical Systems Conference, 2003, 327-330.
Srinivasan, "A Digital Microfluidic Lab-on-a-Chip For Clinical Diagnostic Applications", Ph.D. thesis, Dept of Electrical and Computer Engineering, Duke University, 2005, 136 pages.
Srinivasan et al., "An integrated digital microfluidic lab-on-a-chip for clinical diagnostics on human physiological fluids", Lab on a Chip, vol. 4, 2004, 310-315.
Srinivasan et al., "Clinical diagnostics on human whole blood, plasma, serum, urine, saliva, sweat and tears on a digital microfluidic platform", Proc. 7th International Conference on Micro Total Analysis Systems (mTAS), Squaw Valley, CA, Oct. 5-9, 2003, 1287-1290.
Srinivasan et al., "Digital Microfluidic Lab-on-a-Chip for Protein Crystallization", The 82nd ACS Colloid and Surface Science Symposium, 2008, abstract 452.
Srinivasan et al., "Digital Microfluidics: a novel platform for multiplexed detection of lysosomal storage diseases for newborn screening", AACC Oak Ridge Conference Abstracts, Clinical Chemistry, vol. 54, 2008, poster 78, p. 21.
Srinivasan et al., "Protein Stamping for MALDI Mass Spectrometry Using an Electrowetting-based Microfluidic Platform", Lab-on-a-Chip: Platforms, Devices, and Applications, Conf. 5591, SPIE Optics East, Philadelphia, Oct. 25-28, 2004, 7 pages.
Srinivasan et al., "Scalable Macromodels for Microelectromechanical Systems", Technical Proc. 2001 Int. Conf. on Modeling and Simulation of Microsystems, 2001, 72-75.
Su et al., "Yield Enhancement of Digital Microfluidics-Based Biochips Using Space Redundancy and Local Reconfiguration", Proc. Design, Automation and Test in Europe (DATE) Conf., IEEE, 2005, 1196-1201.
Sudarsan et al., "Printed circuit technology for fabrication of plastic based microfluidic devices", Analytical Chemistry vol. 76, No. 11, Jun. 1, 2004, Previously published online, May 2004, 3229-3235.
Thwar et al., "DNA sequencing using digital microfluidics", Poster 42, 41st AACC's Annual Oak Ridge Conference Abstracts, Clinical Chemistry vol. 55, 2009, 14.
Wang et al., "Droplet-based micro oscillating-flow PCR chip", J. Micromechanics and Microengineering, vol. 15, 2005, 1369-1377.
Wang et al., "Efficient in-droplet separation of magnetic particles for digital microfluidics", Journal of Micromechanics and Microengineering, vol. 17, 2007, 2148-2156.
Xu et al., "A Cross-Referencing-Based Droplet Manipulation Method for High-Throughput and Pin-Constrained Digital Microfluidic Arrays", Proceedings of conference on Design, Automation and Test in Europe (DATE), Apr. 2007, 6 pages.
Xu et al., "Automated Design of Pin-Constrained Digital Microfluidic Biochips Under Droplet-Interference Constraints", ACM Journal on Emerging Technologies is Computing Systems, vol. 3(3), 2007, 14:1-14:23.
Xu et al., "Automated solution preparation on a digital microfluidic lab-on-chip", PSI Bottlenecks Workshop, 2008, 1 page.

(56) References Cited

OTHER PUBLICATIONS

Xu et al., "Automated, Accurate and Inexpensive Solution-Preparation on a Digital Microfluidic Biochip", Proc. IEEE Biomedical Circuits and Systems Conference (BioCAS), 2008, 301-304.

Xu et al., "Defect-Aware Synthesis of Droplet-Based Microfluidic Biochips", IEEE, 20th International Conference on VLSI Design, 2007, 6 pages.

Xu et al., "Design and Optimization of a Digital Microfluidic Biochip for Protein Crystallization", Proc. IEEE/ACM International Conference on Computer-Aided Design (ICCAD), Nov. 2008, 297-301.

Xu et al., "Digital Microfluidic Biochip Design for Protein Crystallization", IEEE-NIH Life Science Systems and Applications Workshop, Lisa, Bethesda, MD, Nov. 8-9, 2007, 140-143.

Xu et al., "Droplet-Trace-Based Array Partitioning and a Pin Assignment Algorithm for the Automated Design of Digital Microfluidic Biochips", CODES, 2006, 112-117.

Xu et al., "Integrated Droplet Routing in the Synthesis of Microfluidic Biochips", IEEE, 2007, 948-953.

Xu et al., "Parallel Scan-Like Test and Multiple-Defect Diagnosis for Digital Microfluidic Biochips", IEEE Transactions on Biomedical Circuits and Systems, vol. 1(2), Jun. 2007, 148-158.

Xu et al., "Parallel Scan-Like Testing and Fault Diagnosis Techniques for Digital Microfluidic Biochips", Proceedings of the 12th IEEE European Test Symposium (ETS), Freiburg, Germany, May 20-24, 2007, 63-68.

Yao et al., "Spot Cooling Using Thermoelectric Microcooler", Proc. 18th Int. Thermoelectric Conf, Baltimore, VA, pp. 256-259, Aug. 1999.

Yi et al., "Channel-to-droplet extractions for on-chip sample preparation", Solid-State Sensor, Actuators and Microsystems Workshop (Hilton Head '06), Hilton Head Island, SC, Jun. 2006, 128-131.

Yi et al., "EWOD Actuation with Electrode-Free Cover Plate", Digest of Tech. papers, 13th International Conference on Solid-State Sensors, Actuators and Microsystems (Transducers '05), Seoul, Korea, Jun. 5-9, 2005, 89-92.

Yi et al., "Geometric surface modification of nozzles for complete transfer of liquid drops", Solid-State Sensor, Actuator and Microsystems Workshop, Hilton Head Island, South Carolina, Jun. 6-10, 2004, 164-167.

Yi, "Soft Printing of Biological Liquids for Micro-arrays: Concept, Principle, Fabrication, and Demonstration", Ph.D. dissertation, UCLA, 2004, 113 pages.

Yi et al., "Soft Printing of Droplets Digitized by Electrowetting", Transducers 12th Int'l Conf. on Solid State Sensors, Actuators and Microsystems, Boston, Jun. 8-12, 2003, 1804-1807.

Yi et al., "Soft Printing of Droplets Pre-Metered by Electrowetting", Sensors and Actuators A: Physical, vol. 114, Jan. 2004, 347-354.

Zeng et al., "Actuation and Control of Droplets by Using Electrowetting-on-Dielectric", Chin. Phys. Lett., vol. 21(9), 2004, 1851-1854.

Zhao et al., "Droplet Manipulation and Microparticle Sampling on Perforated Microfilter Membranes", J. Micromech. Microeng., vol. 18, 2008, 1-11.

Zhao et al., "In-droplet particle separation by travelling wave dielectrophoresis (twDEP) and EWOD", Solid-State Sensor, Actuators and Microsystems Workshop (Hilton Head '06), Hilton Head Island, SC, Jun. 2006, 181-184.

Zhao et al., "Microparticle Concentration and Separation by Traveling-Wave Dielectrophoresis (twDEP) for Digital Microfluidics", J. Microelectromechanical Systems, vol. 16, No. 6, Dec. 2007, 1472-1481.

* cited by examiner

BUBBLE FORMATION TECHNIQUES USING PHYSICAL OR CHEMICAL FEATURES TO RETAIN A GAS BUBBLE WITHIN A DROPLET ACTUATOR

1 RELATED APPLICATIONS

In addition to the patent applications cited herein, each of which is incorporated herein by reference, this patent application is related to and claims priority to U.S. Provisional Patent Application No. 61/146,675, filed on Jan. 23, 2009, entitled "Bubble Techniques for a Droplet Actuator," the entire disclosure of which is incorporated herein by reference.

2 FIELD OF THE INVENTION

The present invention generally relates to the field of conducting droplet operations in a droplet actuator. In particular, the present invention is directed to bubble techniques for a droplet actuator.

3 BACKGROUND OF THE INVENTION

Droplet actuators are used to conduct a wide variety of droplet operations. A droplet actuator typically includes two substrates separated by a gap. The substrates include electrodes for conducting droplet operations. The gap between the substrates is typically filled with a filler fluid that is immiscible with the fluid that is to be subjected to droplet operations. Droplet operations are controlled by electrodes associated with one or both of the substrates. In some applications, one or more bubbles (e.g., gaseous bubbles) may be introduced into a droplet actuator. A bubble can be transported, divided and otherwise manipulated using an actuated fluid (i.e., droplet). The manipulation of a bubble in a droplet actuator can provide additional functionalities to enhance droplet operations. There is a need for efficient methods for generating bubbles and for using bubbles in a droplet actuator.

4 BRIEF DESCRIPTION OF THE INVENTION

The invention provides a droplet actuator and methods of making and using the droplet actuator. In some embodiments, the droplet actuator includes one or more substrates configured to form a droplet operations gap. A physical or chemical feature may be provided at a predetermined locus within or exposed to the droplet operations gap and configured to retain a bubble in position within the droplet operations gap. A bubble may be formed in the droplet operations gap at the chemical or physical feature and surrounded by a liquid filler fluid. Multiple ones of the physical or chemical features may be provided, e.g., an array of the chemical or physical features and an array of bubbles formed in the droplet operations gap and surrounded by a liquid filler fluid. The physical feature may include a recessed region of a surface of the one or more substrates facing the droplet operations gap. The physical feature may include recessed regions of opposing surfaces of the one or more substrates facing the droplet operations gap. The physical feature may include a chemically treated region, such as a chemically etched or roughened feature, of a surface of the one or more substrates facing the droplet operations gap. The physical feature may include a hydrophilic or lipophobic region of a surface of the one or more substrates facing The droplet operations gap. The bubble may span the gap between opposing surfaces of the one or more substrates facing the droplet operations gap. The bubble may include a gaseous bubble substantially surrounded by oil within the droplet operations gap. The bubble may include a gaseous bubble at least partially surrounded by oil within the droplet operations gap. In some cases, the bubble is partly surrounded by oil and partly surrounded by one or more droplet actuator components or surfaces. The filler fluid may include oil. The filler fluid may include low viscosity oil. The filler fluid may include low viscosity oil doped with a surfactant. The one or more substrates of the droplet actuator may, in some embodiments, include a top substrate and a bottom substrate. The bottom substrate may be separated from the top substrate by a gap. The gap may, for example, be defined by a spacer. The recessed region, when present, may be on the top substrate facing the bottom substrate, and the bottom substrate further may include a recessed region opposite to the recessed region of the top substrate. The recessed region may be formed by a technique including patterning, embossing and/or etching. The top substrate recessed region and bottom substrate recessed region are of sufficient depth to form a bubble as filler fluid may be flowed into the gap, and for retaining a bubble in position in the gap. The recessed region may be provided only in the top substrate. The recessed region may be provided only in the bottom substrate. The droplet actuator may include a fluid reservoir formed in the droplet operations gap and including the bubble, the fluid reservoir including fluid barriers which at least partially surround the bubble. The droplet actuator may include a path of electrodes arranged for transporting a droplet situated in the droplet operations gap into the reservoir. The bubble may be arranged to restrain movement of a droplet in the filler fluid. The droplet actuator may include a fluid path arranged for flowing fluid from a source which may be external to the droplet operations gap into the bubble. The droplet actuator may include a dried reagent situated within the gaseous bubble. The droplet actuator may include an array of dried reagent, each dried reagent situated within a gaseous bubble in the array of bubbles. The bubble may include a preselected gas composition. The bubble may include a preselected gas composition that may be not air. The bubble consists substantially of a single gas or of a mixture of gases. The bubble may be composed of air. The bubble may be formed under pressure. The droplet actuator may be operated under pressure. The droplet actuator may include a temperature control element arranged to control temperature of the bubble. The droplet actuator may be operated in a temperature controlled chamber. The droplet actuator may include one or more physical barriers arranged to restrain movement of the bubble.

The invention provides a method of forming a bubble in a droplet actuator. The method may include providing the droplet actuator as described herein, and dispensing filler fluid into the droplet operations gap at a rate and volume sufficient to fill the fluid reservoir and form an gaseous bubble at the physical and/or chemical feature. Alternatively, the invention provides a method of providing a droplet actuator including a bubble in a droplet operations gap thereof, the method including: forming a gaseous bubble in a droplet operations gap of a droplet actuator, wherein the bubble may be at least partially surrounded by a filler fluid and, optionally, partially surrounded by one or more droplet actuator surfaces; and forming a droplet in the filler fluid, wherein the droplet may be substantially immiscible with and surrounded by the filler fluid. In the various methods provided, the bubble may be compressed within the droplet operations gap. The bubble may be compressed within the droplet operations gap and may be substantially discoid in shape. The method may include transporting the droplet from the filler fluid into the bubble. The droplet may be compressed within the droplet operations gap such that the droplet may be substantially discoid in shape.

The method may include providing a dried reagent in the bubble. The method may include transporting the droplet actuator including the dried reagent in the bubble. The method may include reconstituting the dried reagent in the bubble. The method may include transporting a droplet from the filler fluid into the bubble to reconstitute the dried reagent. Transporting the droplet from the filler fluid into the bubble may be mediated by electrodes associated with a substrate of the droplet actuator. Forming a gaseous bubble in a droplet operations gap of a droplet actuator may include flowing a filler fluid into a droplet operations gap including features selected to cause formation of a bubble in the droplet operations gap at a predetermined locus. The method may include subjecting the droplet to one or more droplet operations within the bubble. The bubble may include a preselected gas composition. The bubble consists substantially of a single gas. The bubble may be formed under pressure. The method may include evaporating the droplet within the bubble. The method may include evaporating a portion of the droplet to concentrate one or more components in the droplet. The droplet actuator may include one or more physical barriers in the reservoir for supporting and retaining the bubble in the reservoir. The method may include flowing the bubble out of the droplet operations gap. The method may include flowing the bubble into a different region of the droplet operations gap. The method may include using the bubble to prevent movement of the droplet. ps 5 Definitions As used herein, the following terms have the meanings indicated.

"Activate" with reference to one or more electrodes means effecting a change in the electrical state of the one or more electrodes which, in the presence of a droplet, results in a droplet operation.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical and other three dimensional shapes. The bead may, for example, be capable of being transported in a droplet on a droplet actuator or otherwise configured with respect to a droplet actuator in a manner which permits a droplet on the droplet actuator to be brought into contact with the bead, on the droplet actuator and/or off the droplet actuator. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead or one component only of a bead. The remainder of the bead may include, among other things, polymeric material, coatings, and moieties which permit attachment of an assay reagent. Examples of suitable magnetically responsive beads are described in U.S. Patent Publication No. 2005-0260686, entitled, "Multiplex flow assays preferably with magnetic particles as solid phase," published on Nov. 24, 2005, the entire disclosure of which is incorporated herein by reference for its teaching concerning magnetically responsive materials and beads. The fluids may include one or more magnetically responsive and/or non-magnetically responsive beads. Examples of droplet actuator techniques for immobilizing magnetically responsive beads and/or non-magnetically responsive beads and/or conducting droplet operations protocols using beads are described in U.S. patent application Ser. No. 11/639,566, entitled "Droplet-Based Particle Sorting," filed on Dec. 15, 2006; U.S. Patent Application No. 61/039,183, entitled "Multiplexing Bead Detection in a Single Droplet," filed on Mar. 25, 2008; U.S. Patent Application No. 61/047,789, entitled "Droplet Actuator Devices and Droplet Operations Using Beads," filed on Apr. 25, 2008; U.S. Patent Application No. 61/086,183, entitled "Droplet Actuator Devices and Methods for Manipulating Beads," filed on Aug. 5, 2008; International Patent Application No. PCT/US2008/053545, entitled "Droplet Actuator Devices and Methods Employing Magnetic Beads," filed on Feb. 11, 2008; International Patent Application No. PCT/US2008/058018, entitled "Bead-based Multiplexed Analytical Methods and Instrumentation," filed on Mar. 24, 2008; International Patent Application No. PCT/US2008/058047, "Bead Sorting on a Droplet Actuator," filed on Mar. 23, 2008; and International Patent Application No. PCT/US2006/047486, entitled "Droplet-based Biochemistry," filed on Dec. 11, 2006; the entire disclosures of which are incorporated herein by reference.

"Droplet" means a volume of liquid on a droplet actuator that is at least partially bounded by filler fluid. For example, a droplet may be completely surrounded by filler fluid or may be bounded by filler fluid and one or more surfaces of the droplet actuator. Droplets may, for example, be aqueous or non-aqueous or may be mixtures or emulsions including aqueous and non-aqueous components. Droplets may take a wide variety of shapes; nonlimiting examples include generally disc shaped, slug shaped, truncated sphere, ellipsoid, spherical, partially compressed sphere, hemispherical, ovoid, cylindrical, and various shapes formed during droplet operations, such as merging or splitting or formed as a result of contact of such shapes with one or more surfaces of a droplet actuator. For examples of droplet fluids that may be subjected to droplet operations using the approach of the invention, see International Patent Application No. PCT/US 06/47486, entitled, "Droplet-Based Biochemistry," filed on Dec. 11, 2006. In various embodiments, a droplet may include a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes. Moreover, a droplet may include a reagent, such as water, deionized water, saline solutions, acidic solutions, basic solutions, detergent solutions and/or buffers. Other examples of droplet contents include reagents, such as a reagent for a biochemical protocol, such as a nucleic acid amplification protocol, an affinity-based assay protocol, an enzymatic assay protocol, a sequencing protocol, and/or a protocol for analyses of biological fluids.

"Droplet Actuator" means a device for manipulating droplets. For examples of droplet actuators, see U.S. Pat. No. 6,911,132, entitled "Apparatus for Manipulating Droplets by Electrowetting-Based Techniques," issued on Jun. 28, 2005 to Pamula et al.; U.S. patent application Ser. No. 11/343,284, entitled "Apparatuses and Methods for Manipulating Droplets on a Printed Circuit Board," filed on filed on Jan. 30, 2006; U.S. Pat. Nos. 6,773,566, entitled "Electrostatic Actuators for Microfluidics and Methods for Using Same," issued on Aug. 10, 2004 and 6,565,727, entitled "Actuators for Microfluidics Without Moving Parts," issued on Jan. 24, 2000, both to Shenderov et al.; Pollack et al., International Patent Application No. PCT/US2006/047486, entitled "Droplet-Based Biochemistry," filed on Dec. 11, 2006, the disclosures of which are incorporated herein by reference. Methods of the invention may be executed using droplet actuator systems, e.g., as described in International Patent Application No. PCT/US2007/009379, entitled "droplet manipulation systems," filed on May 9, 2007. In various embodiments, the manipulation of droplets by a droplet actuator may be electrode mediated, e.g., electrowetting mediated or dielectrophoresis mediated. Examples of other methods of controlling fluid flow that may be used in the droplet actuators of the invention include devices that induce hydrodynamic fluidic pressure, such as those that operate on the basis of mechanical principles (e.g. external syringe pumps, pneumatic membrane pumps, vibrating membrane pumps, vacuum devices, centrifugal forces, and capillary action); electrical or magnetic principles (e.g. electroosmotic flow, electrokinetic pumps piezoelectric/ultrasonic pumps, ferrofluidic plugs, electrohydrodynamic pumps, and magnetohydrodynamic pumps); thermodynamic principles (e.g. gaseous bubble generation/phase-change-induced volume expansion); other kinds of surface-wetting principles (e.g. electrowetting, and optoelectrowetting, as well as chemically, thermally, and radioactively induced surface-tension gradient); gravity; surface tension (e.g., capillary action); electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential. In certain embodiments, combinations of two or more of the foregoing techniques may be employed in droplet actuators of the invention.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to volume of the resulting droplets (i.e., the volume of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. Droplet operations may be electrode-mediated. In some cases, droplet operations are further facilitated by the use of hydrophilic and/or hydrophobic regions on surfaces and/or by physical obstacles.

"Filler fluid" means a fluid associated with a droplet operations substrate of a droplet actuator, which fluid is sufficiently immiscible with a droplet phase to render the droplet phase subject to electrode-mediated droplet operations. The filler fluid may, for example, be a low-viscosity oil, such as silicone oil. Other examples of filler fluids are provided in International Patent Application No. PCT/US2006/047486, entitled, "Droplet-Based Biochemistry," filed on Dec. 11, 2006; and in International Patent Application No. PCT/US2008/072604, entitled "Use of additives for enhancing droplet actuation," filed on Aug. 8, 2008. The filler fluid may fill the entire gap of the droplet actuator or may coat one or more surfaces of the droplet actuator.

"Immobilize" with respect to magnetically responsive beads, means that the beads are substantially restrained in position in a droplet or in filler fluid on a droplet actuator. For example, in one embodiment, immobilized beads are sufficiently restrained in position to permit execution of a splitting operation on a droplet, yielding one droplet with substantially all of the beads and one droplet substantially lacking in the beads.

"Magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, $CoO$, $NiO$, $Mn_2O_3$, $Cr_2O_3$, and $CoMnP$.

"Washing" with respect to washing a magnetically responsive bead means reducing the amount and/or concentration of one or more substances in contact with the magnetically responsive bead or exposed to the magnetically responsive bead from a droplet in contact with the magnetically responsive bead. The reduction in the amount and/or concentration of the substance may be partial, substantially complete, or even complete. The substance may be any of a wide variety of substances; examples include target substances for further analysis, and unwanted substances, such as components of a sample, contaminants, and/or excess reagent. In some embodiments, a washing operation begins with a starting droplet in contact with a magnetically responsive bead, where the droplet includes an initial amount and initial concentration of a substance. The washing operation may proceed using a variety of droplet operations. The washing operation may yield a droplet including the magnetically responsive bead, where the droplet has a total amount and/or concentration of the substance which is less than the initial amount and/or concentration of the substance. Examples of suitable washing techniques are described in Pamula et al., U.S. Pat. No. 7,439,014, entitled "Droplet-Based Surface Modification and Washing," granted on Oct. 21, 2008, the entire disclosure of which is incorporated herein by reference.

The terms "top," "bottom," "over," "under," and "on" are used throughout the description with reference to the relative positions of components of the droplet actuator, such as relative positions of top and bottom substrates of the droplet actuator. It will be appreciated that the droplet actuator is functional regardless of its orientation in space.

When a liquid in any form (e.g., a droplet or a continuous body, whether moving or stationary) is described as being "on", "at", or "over" an electrode, array, matrix or surface, such liquid could be either in direct contact with the electrode/ array/matrix/surface, or could be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

6 BRIEF DESCRIPTION OF THE DRAWINGS

7 DETAILED DESCRIPTION OF THE INVENTION

Figure 1:
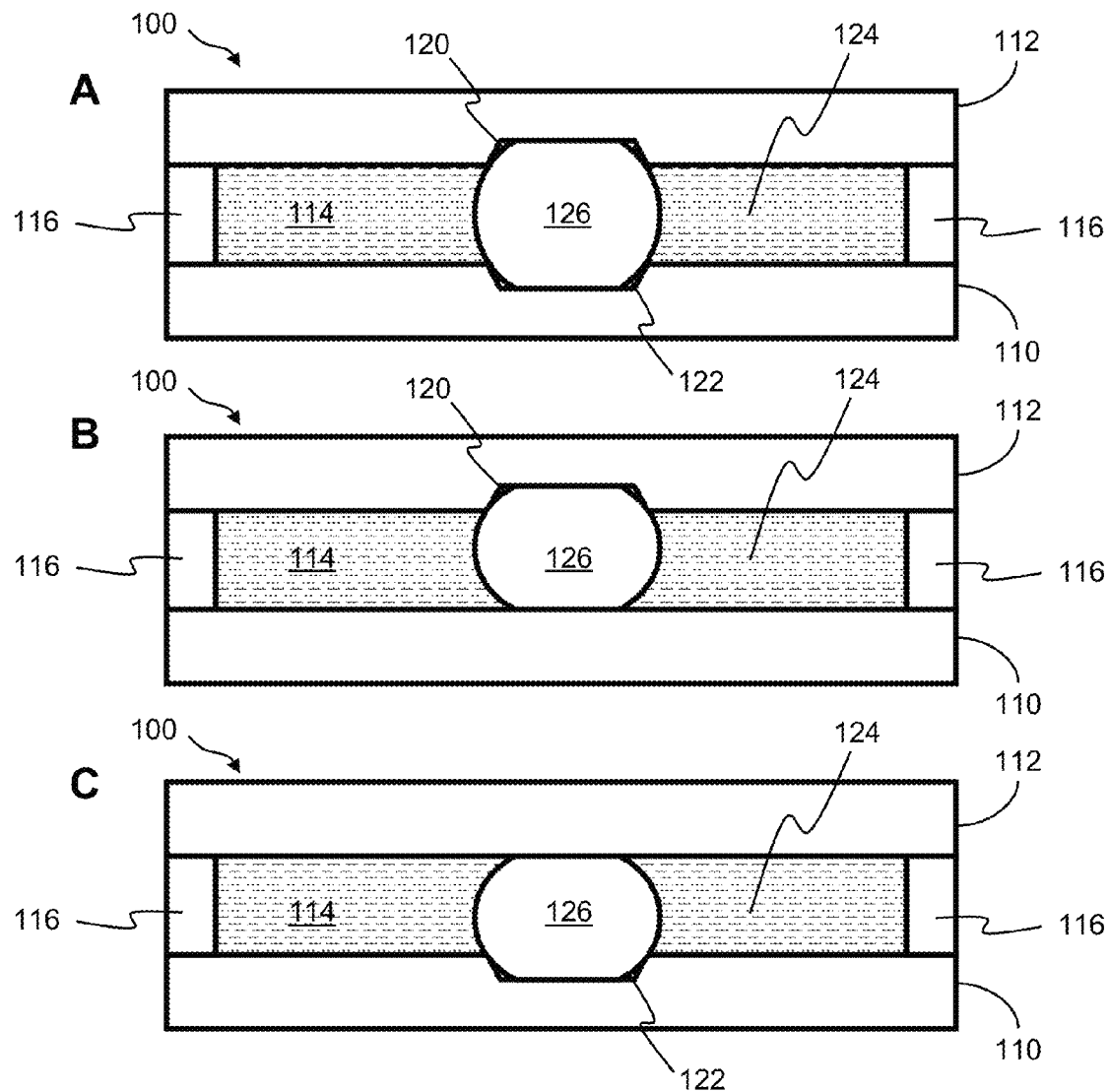
FIGS. 1A through 1C illustrate side views of a portion of a droplet actuator and a method of forming bubbles on a droplet actuator.

The invention provides methods of generating bubbles on a droplet actuator and for using bubbles to facilitate droplet operations and bubble operations. The invention provides methods for transporting a droplet into a bubble and/or splitting a bubble. The invention also provides techniques for using a bubble to provide for gas exchange within a droplet or fluid. Further, the invention provides methods for using bubbles to provide a barrier to fluids and/or droplets in a droplet actuator. In one embodiment, a bubble provides a barrier function that may be used, for example, to prevent the movement of a droplet or fluid in the absence of active droplet operations forces. In another embodiment, a bubble provides a barrier function that may be used, for example, as a reversible and/or non-reversible gating mechanism. These and other embodiments will be apparent from the ensuing discussion.

7.1 Bubble Formation

FIGS. 1A through 1C illustrate sectional side views of a droplet actuator 100 and illustrate a method of forming a bubble on a droplet actuator and/or maintaining a bubble in a location on a droplet actuator. The method of the invention of FIGS. 1A through 1C uses recessed regions on top and/or bottom substrates and capillary action of a filler fluid to trap bubbles (e.g., gaseous bubbles or air pockets) within the recessed regions. A process of forming a controllable bubble is described in more detail with reference to FIGS. 3A through 3D.

Referring to FIG. 1A, droplet actuator 100 may include a bottom substrate 110 and a top substrate 112. Bottom substrate 110 may be separated from top substrate 112 by a gap 114. A spacer 116 may be used to determine the size of gap 114. A recessed region 120 may be provided on top substrate 112. A recessed region 122 may be provided on bottom substrate 110. Recessed region 122 may be substantially aligned with recessed region 120. Recessed region 120 and 122 may, for example, be formed using techniques such as patterning, embossing, and etching. Recessed regions 120 and 122 are of sufficient depth (e.g., about 10-25 μm) to form a bubble as filler fluid 124 is flowed into the gap and/or to retain a bubble in position in the gap. The presence of recessed region 120 and/or 122 serves to expand the height of gap 114 in a localized location only along droplet actuator 100.

Gap 114 is filled with a filler fluid 124. Filler fluid 124 may, for example, be low-viscosity oil, such as silicone oil. Filler fluid 124 fills gap 114 by capillary action such that a bubble 126 is formed in the expanded area of gap 114 that is formed by recessed region 120 and recessed region 122. Filler fluid 124 may be doped with a surfactant.

In another embodiment, droplet actuator 100 may include a recessed region for forming bubbles in one substrate only. FIG. 1B shows a droplet actuator with recessed region 120 in top substrate 112 only and no recessed region 122 in bottom substrate 110. FIG. 1C shows recessed region 122 in bottom substrate 110 only and no recessed region 120 in top substrate 112.

The placement of one or more recessed regions 120 and/or recessed regions 122 may be at any location(s) along gap 114 of droplet actuator 100 for the controllable formation and/or retention of bubbles in the droplet actuator.

Figure 2:
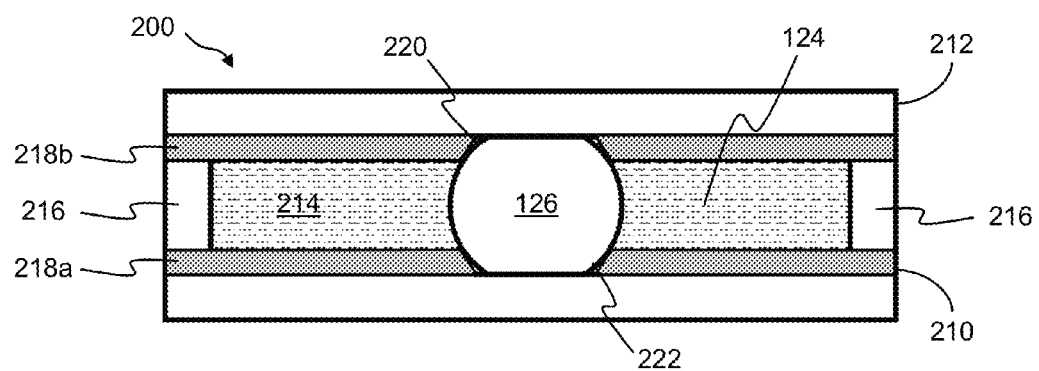
FIG. 2 illustrates a side view of a portion of a droplet actuator and shows another way of forming recessed regions for forming a controllable bubble.

FIG. 2 illustrates a sectional side view of a portion of a droplet actuator 200. Droplet actuator 200 may include a bottom substrate 210 and a top substrate 212. Bottom substrate 210 may be separated from top substrate 212 by a gap 214. A spacer 216 may be used to determine the size of gap 214. A layer of material 218, such as gasket material, may be provided atop bottom substrate 210 and/or top substrate 212. In one example, a layer of material 218a is atop bottom substrate 210 and/or a layer of material 218b is atop substrate 212. A clearance region is formed in material 218a and/or material 218b in order to create a recessed region 220 and/or a recessed region 222. In this embodiment, recessed region 220 and/or 222 may be formed without the need to pattern, emboss, etch, and/or otherwise process bottom substrate 210 and/or top substrate 212. With respect to forming a controllable bubble, droplet actuator 200 that includes recessed region 220 and/or 222 is substantially the same as droplet actuator 100 of FIGS. 1A, 1B, and 1C.

FIGS. 3A through 3D illustrate top views of a fluid reservoir 300 of a portion of a droplet actuator. In this embodiment, fluid reservoir 300 is used to illustrate the process of forming a controllable bubble. Fluid reservoir 300 may be formed between two substrates (not shown) of a droplet actuator. The substrates are separated by a gap. The boundaries of fluid reservoir 300 may be formed by a barrier 312, which may be, for example, gasket material or another substrate material. A recessed region 314 may be disposed within fluid reservoir 300 for controllably forming a bubble. Recessed region 314 may, for example, be formed on the bottom and/or top substrates as described in reference to FIGS. 1A through 1C. An opening 316 may, for example, be an opening in the substrate of the droplet actuator through which a fluid, such as a filler fluid 318, may be loaded into fluid reservoir 300. Opening 316 may be of any suitable size, shape, and/or geometry.

As shown in FIGS. 3A, 3B, and 3C, as filler fluid 318 is dispensed through opening 316 and flows into fluid reservoir 300, filler fluid 318 flows (e.g., capillary action) around recessed region 314. This is because filler fluid 318 preferentially flows in the smaller gaps of fluid reservoir 300 and, thus, tends to flow in the regions around recessed region 314 where the gap height is less than within recessed region 314. As a result, as filler fluid 318 fills fluid reservoir 300, an gaseous bubble 320 is formed in recessed region 314, as shown in FIG. 3D. Any number of gaseous bubbles may be formed in this manner.

7.2 Transporting a Droplet into a Bubble

Figure 3:
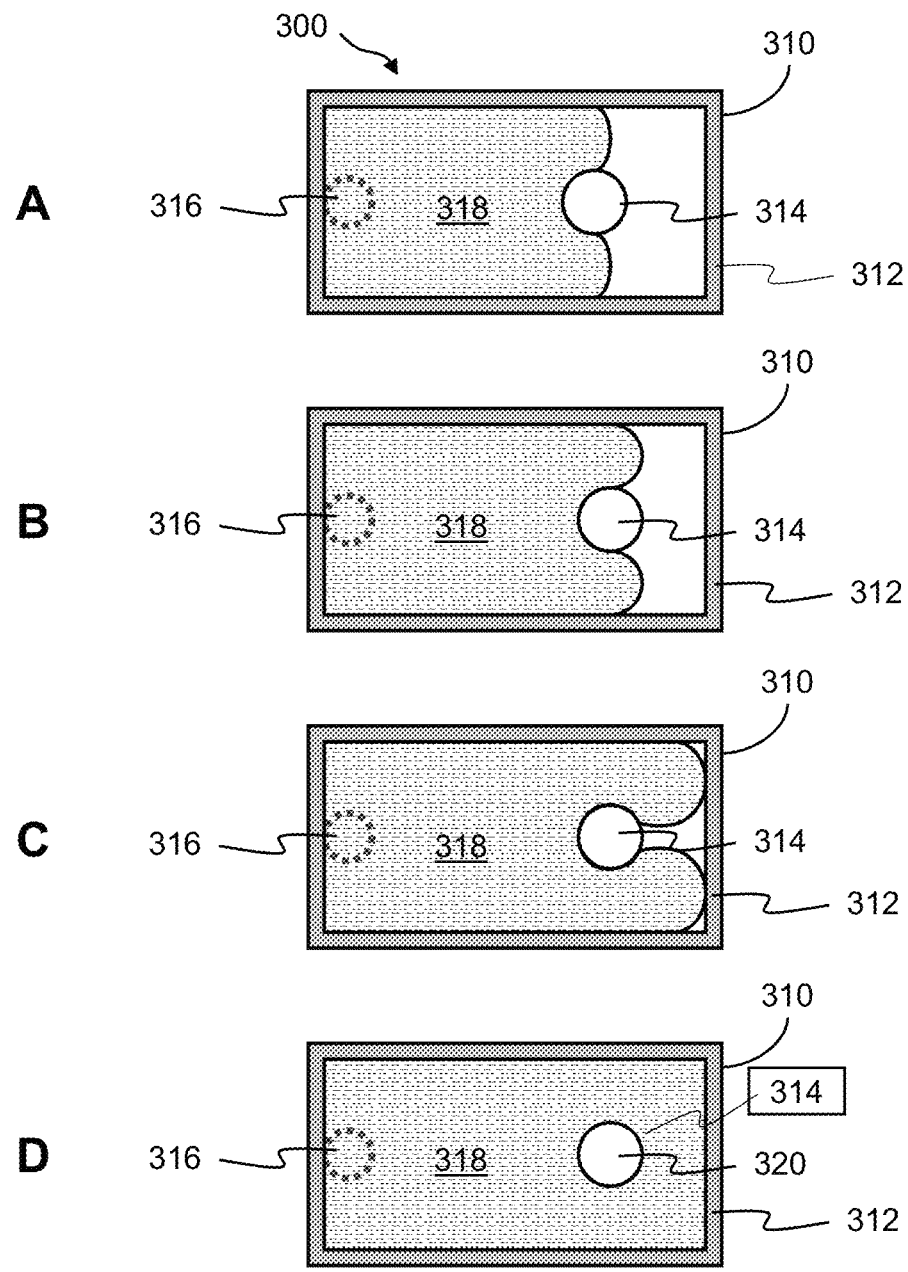
FIGS. 3A through 3D illustrate top views of a fluid reservoir of a portion of a droplet actuator.
Figure 4:
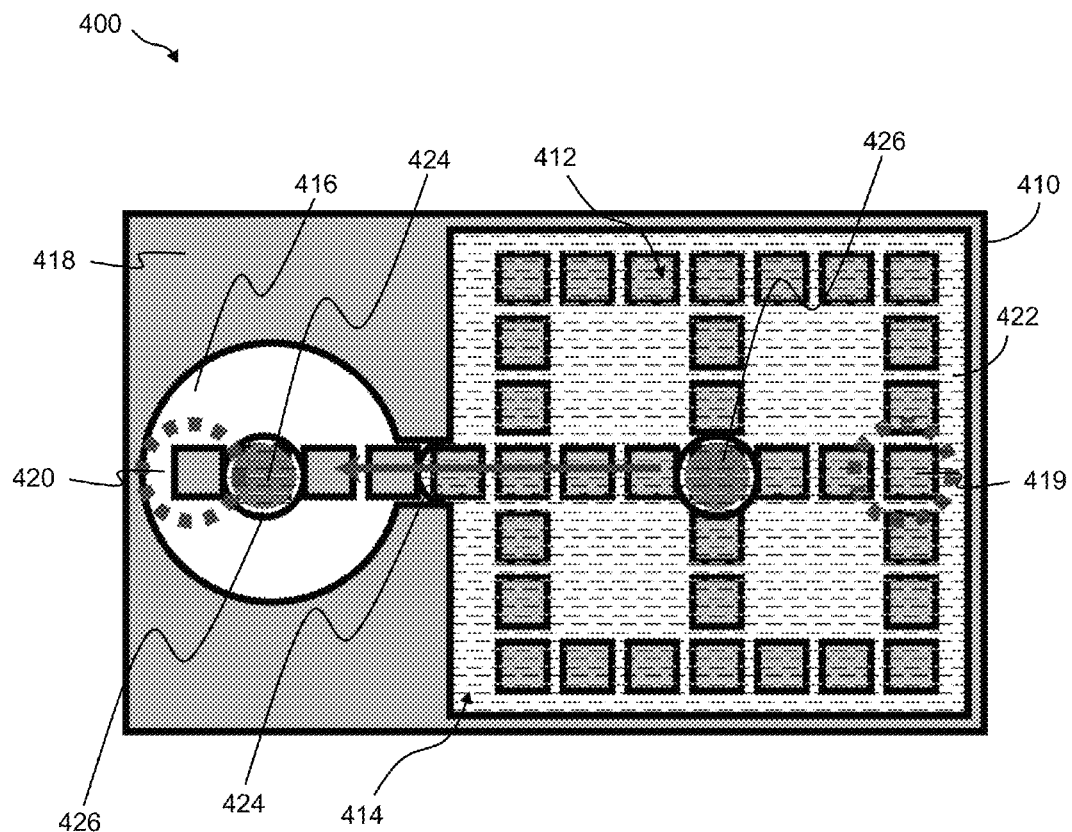
FIG. 4 illustrates a top view of a portion of a droplet actuator and shows a process of transporting a droplet into an gaseous bubble within a reservoir.

FIG. 4 illustrates a top view of a portion of a droplet actuator 400 and shows a process of transporting a droplet into an gaseous bubble within a reservoir. Droplet actuator 400 may include a bottom substrate 410 separated from a top substrate (not shown) by a gap. Bottom substrate 410 may include a path or array of droplet operations electrodes 412 (e.g., electrowetting electrodes) in a droplet operations region 414. The droplet operations region 414 may feed a reservoir 416 that is formed within a layer of material 418 on bottom substrate 410. Material 418 may be, for example, a layer of gasket material. Reservoir 416 may have a depth of, for example, about 200-300 µm. Droplet actuator 400 may include a fluid inlet 419 and a fluid outlet 420. Fluid inlet 419 may be an opening through which a filler fluid 422, such as an oil filler fluid, may be loaded into droplet actuator 400. Fluid outlet 420 may be sealed such that as filler fluid 422 is loaded into droplet actuator 400, an gaseous bubble is trapped within reservoir 416 as described with reference to FIG. 3. An oil/air interface 424 may be formed at the narrow opening of reservoir 416.

Droplet actuator 400 may include a droplet 426 that may be formed of a liquid (e.g., an aqueous liquid) that is immiscible with filler fluid 422 (e.g., oil). Droplet 426 may be transported along droplet operations electrodes 412 of droplet operations region 414 toward reservoir 416, thereby moving droplet 426 into the gaseous bubble within reservoir 416. As droplet 426 is transported across oil/air interface 424 into the gaseous bubble in reservoir 416, a small amount of filler fluid 422 that surrounds droplet 426 may be also be transported and pinched-off. As a result, droplet 426 may be encased in a small amount of filler fluid 422 and, thus, droplet 426 is surrounded by an oil layer and air. The oil layer may be removed from droplet 426 by, for example, heating (not shown).

In another embodiment, a droplet transported into an gaseous bubble may be concentrated by heating. For example, in a molecular assay, such as polymerase chain reaction (PCR), a droplet within an gaseous bubble may be heated for a sufficient period of time to cause the water in the droplet evaporates into the gaseous bubble. As the volume of the droplet decreases, the concentration of reaction components within the droplet increases and the volume of the gaseous bubble increases.

Figure 5:
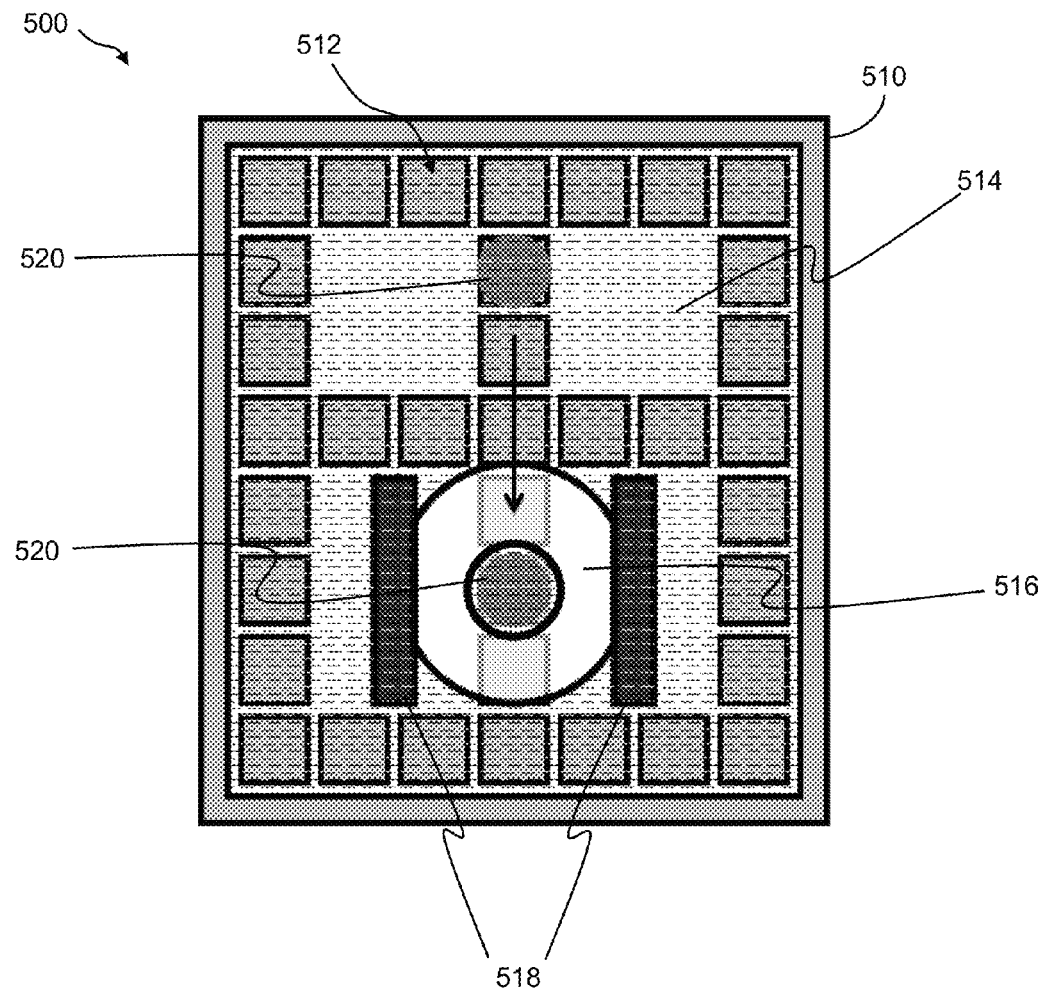
FIG. 5 illustrates a top view of a portion of a droplet actuator and shows a process of transporting a droplet into an gaseous bubble within an array of droplet operation electrodes.

FIG. 5 illustrates a top view of a portion of a droplet actuator 500 and shows a process of transporting a droplet into an gaseous bubble within an array of droplet operation electrodes. Droplet actuator 500 may include a bottom substrate 510 separated from a top substrate (not shown) by a gap. Bottom substrate 510 may include a path or array of droplet operations electrodes 512 (e.g., electrowetting electrodes). A filler fluid 514, such as an oil filler fluid, may be loaded into the gap of droplet actuator 500. An gaseous bubble 516 may be formed in proximity of specific droplet operations electrodes 512. Gaseous bubble 516 may, for example, be formed in a recessed region as described above with reference to FIG. 1 and FIG. 2. Gaseous bubble 516 may in some embodiments be further supported and/or retained to specific droplet operations electrodes 512 by a pair of physical barriers 518. Barriers 518 may be, for example, a solid material, such as a gasket material.

A droplet 520 within droplet actuator 500 may be transported along droplet operations electrodes 512 toward and into gaseous bubble 516. Droplet 520 may be formed of a liquid (e.g., an aqueous liquid) that is immiscible with filler fluid 514 (e.g., oil). As droplet 520 is transported into gaseous bubble 516, droplet 520 may be encased in a small amount of filler fluid 514 and, thus, droplet 520 is surrounded by an oil layer and air.

In one embodiment, a bubble may be used to provide oxygen to a droplet or liquid in a reservoir. A droplet may be transported to a bubble to allow gas exchange, e.g., oxygenation of the droplet and/or escape of $CO_2$ from the droplet (or vice versa). Gas exchange may be useful for supporting live cells within a droplet and/or accomplishing chemical reactions. A series of merge and split operations may be used to repeatedly aerate a droplet. In another embodiment, a bubble may be used to perform gas-liquid extractions. For example, breath analysis could be performed by a gas to droplet exchange.

7.3 Bubble-Based Barrier and Gating Mechanisms

Figure 6:
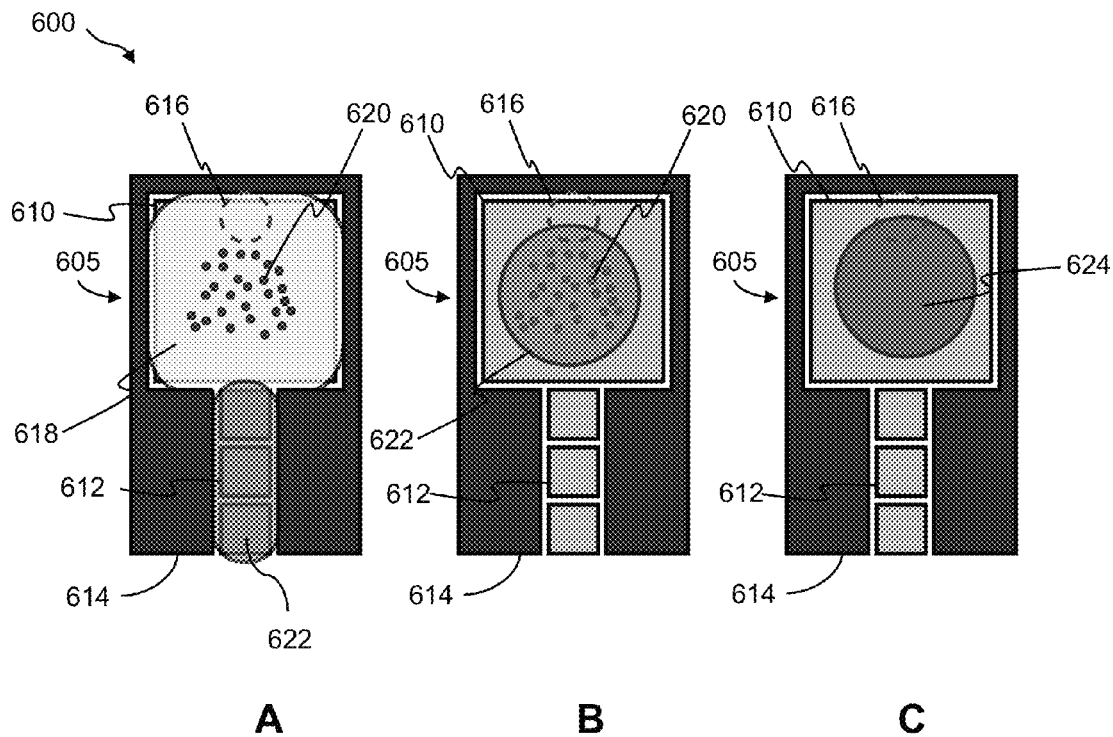
FIGS. 6A through 6C illustrate top views of a portion of a droplet actuator and show a process of reconstituting a dried reagent in a reservoir.

FIGS. 6A through 6C illustrate top views of a portion of a droplet actuator 600 and show a process of reconstituting a dried reagent in a reservoir. The method of the invention of FIG. 6 is an example of a method of reagent storage, wherein an gaseous bubble is used to prevent a fluid from entering a reservoir and contaminating a dried reagent. Droplet actuator 600 may be formed by two substrates (not shown) that are separated by a gap. A reservoir 605 may be formed between the two substrates of droplet actuator 600. A reservoir electrode 610 may be associated with reservoir 605. A path or line of droplet operations electrodes 612 (e.g., electrowetting electrodes) may feed reservoir 605. Reservoir 605 and droplet operations electrodes 612 may be bounded by, for example, gasket material 614, which may be in the gap of droplet actuator 600. An opening 616 in a top substrate (not shown) may be provided in proximity to reservoir electrode 610. Opening 616 may be sealed to facilitate formation of an gaseous bubble 618, which may be air that is trapped within reservoir 605. Reservoir 605 may include an amount of a dried reagent 620 deposited on reservoir electrode 610. Initially, dried reagent 620 may be maintained in a dried state because it is encapsulated within gaseous bubble 618.

FIG. 6A shows the first step in a process of reconstituting a dried reagent in a reservoir. In this step, a droplet 622 is positioned at droplet operations electrodes 612. Droplet 622 may, for example, be a buffer suitable for reconstituting (solubilizing) dried reagent 620. Gaseous bubble 618 prevents droplet 622 from entering reservoir 605 and contaminating dried reagent 620. This state may be maintained, for example, during storage and/or transport of a droplet actuator prior to use.

FIG. 6B shows another step in the process of reconstituting a dried reagent in a reservoir. In this step, opening 616 is punctured, which allows air of gaseous bubble 618 to escape from reservoir 605. As a result, droplet 622 is allowed to displace gaseous bubble 618 as it is transported to reservoir electrode 610 via droplet operations. This step may, for example, be effected by a user prior to execution of an assay protocol using the droplet actuator.

FIG. 6C shows another step in the process of reconstituting a dried reagent in a reservoir. In this step, droplet 622 has partially, preferably fully, displaced gaseous bubble 618 in reservoir 605. Consequently, droplet 622 combines with dried reagent 620 to yield a reconstituted reagent 624 (i.e., dried reagent 620 is solubilized in fluid 622). Reconstituted reagent 624 is suitable for use in droplet actuator-based assay protocols. For example, reconstituted reagent 624 may be a reagent for an immunoassay.

Figure 7:
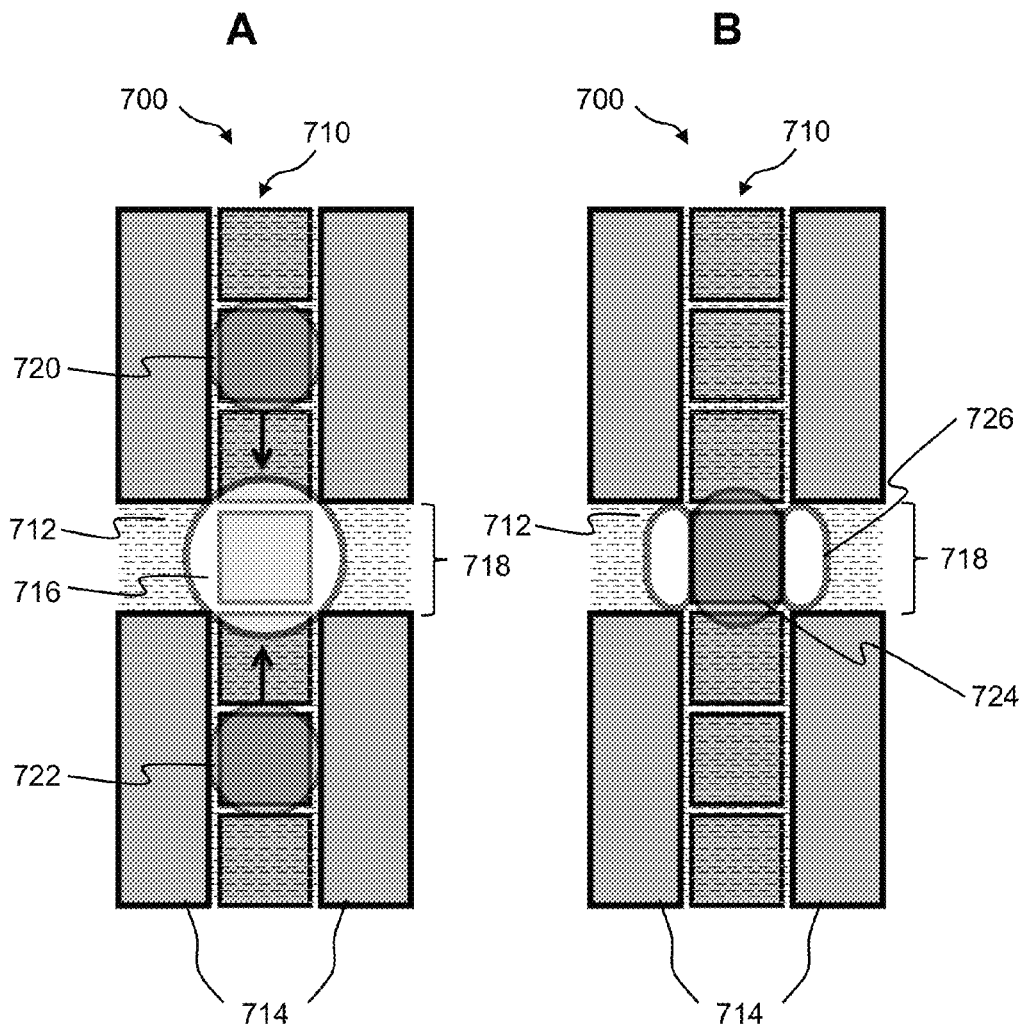
FIGS. 7A and 7B illustrate top views of a portion of a droplet actuator and show a process of splitting a bubble.

FIGS. 7A and 7B illustrate top views of a portion of a droplet actuator 700 and show a process of splitting a bubble. The method of the invention of FIG. 7 provides, among other things, a bubble-based gating mechanism wherein the merging of two droplets is used to split a small bubble-based gate and form a stable split bubble. Droplet actuator 700 may include a path or array of droplet operations electrodes 710 formed between two substrates (not shown) that are separated by a gap. A filler fluid 712, such as an oil filler fluid, may be loaded into the gap of droplet actuator 700. Certain barriers 714, such as barriers formed of gasket material, are provided along droplet operations electrodes 710. Barriers 714 may bound the line of droplet operations electrodes 710, except at a location of one or more droplet operations electrodes 710 that may be designated for retaining a bubble 716. As a result, bubble 716 may be in the path of droplet operations electrodes 710. Recessed regions 718, such as described in FIGS. 1 through 3, may be provided in the regions on both sides of the designated droplet operations electrode 710.

FIG. 7A shows the first step in a process of splitting a bubble to open a bubble-based gate or valve. In this step, bubble 716 is positioned at the designated droplet operations electrode 710. A first droplet 720 and a second droplet 722 are provided on opposite sides of bubble 716 along droplet operations electrodes 710. In this way, bubble 716 is initially sandwiched between droplet 720 and droplet 722. Droplet 720 and droplet 722 are then transported via droplet operations toward bubble 716.

FIG. 7B shows another step in a process of splitting a bubble to open a bubble-based gate or valve. In this step, droplet 720 and droplet 722 are merged using droplet operations to form a merged droplet 724. As droplet 720 and droplet 722 are merged into a larger droplet 724 at the designated droplet operations electrode 710, bubble 716 is split into two smaller bubbles 726. Consequently, the two smaller bubbles 726 are squeezed into the adjacent areas 718 that are on respective sides of the designated droplet operations electrode 710. In embodiments in which the adjacent areas 718 are depressed areas, the two smaller bubbles 726 are stable, i.e., they do not rebound back onto the designated droplet operations electrode 710 when droplet 724 is removed.

In another embodiment, a recessed region is provided at the designated droplet operations electrode 710 instead of on both sides. Therefore, the two displaced smaller bubbles 726 may return to the original position and remerge into one bubble after droplet 724 is transported away from the designated droplet operations electrode 710.

In yet another embodiment, a bubble-based gating mechanism may be used to suppress the flow of oil in a channel until a droplet is transported through.

In still another embodiment, a bubble may function as a dynamic barrier. In this example, a droplet may be used to move a bubble along droplet operations electrodes to different positions within a droplet actuator. The droplet may force the bubble along droplet operations electrodes, e.g., through a channel without splitting and/or displacing the bubble. If desired, the bubble may be delivered in this manner into a recessed region, where it may perform one or more of the various functions described herein.

Figure 8:
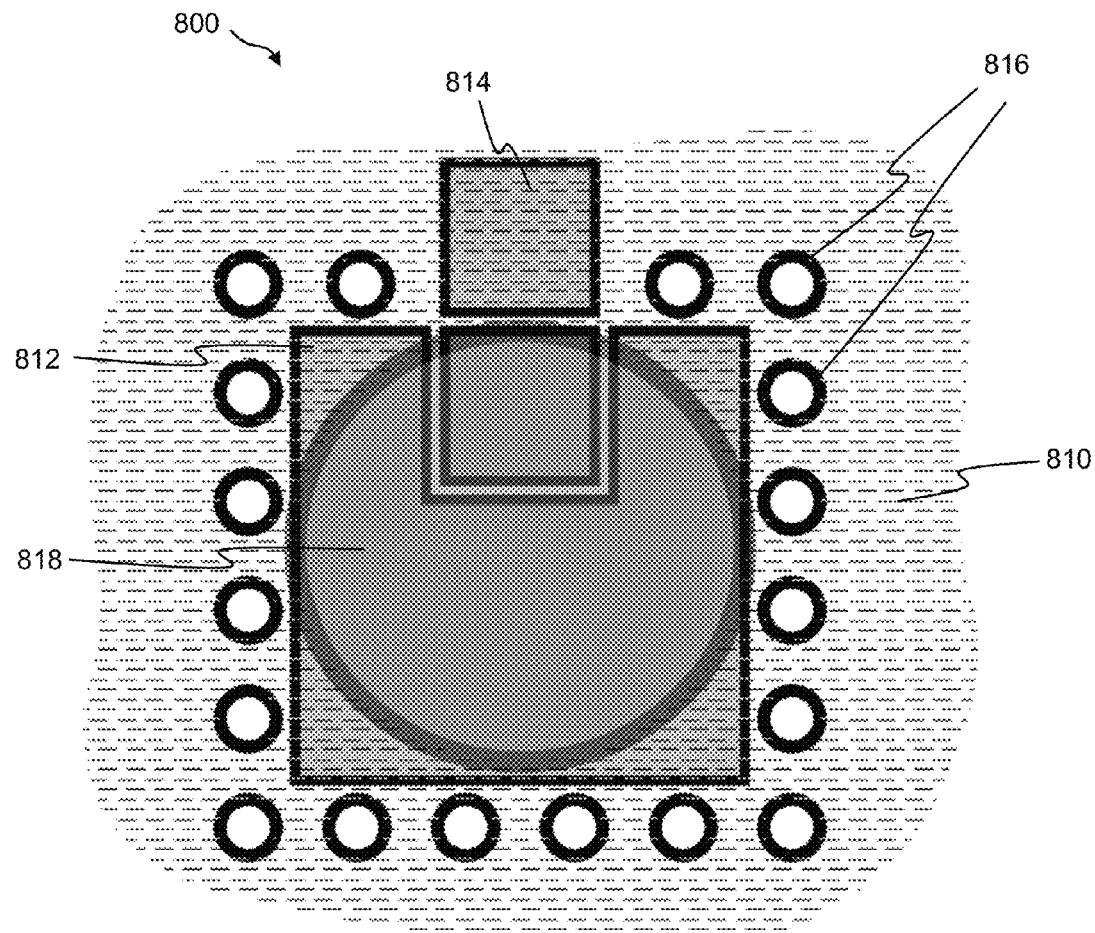
FIG. 8 illustrates a top view of a reservoir of a droplet actuator and a method of providing a barrier to a fluid in a reservoir.

FIG. 8 illustrates a top view of a reservoir 800 of a droplet actuator and a method of providing a barrier to a fluid in a reservoir. The method of the invention of FIG. 8 is an example of a method of providing a barrier to a fluid in a reservoir wherein a series of gaseous bubbles function as a "gasket." Reservoir 800 may be formed between two substrates (not shown) of a droplet actuator. The two substrates are separated by a gap. A filler fluid 810, such as an oil filler fluid, may be loaded into the gap of the droplet actuator. A reservoir electrode 812 may be associated with reservoir 800. Reservoir electrode 812 may feed an arrangement of droplet operations electrodes 814. A series of bubbles 816 (e.g., gaseous bubbles) may be formed around reservoir electrode 812. For example, bubbles 816 may be arranged around reservoir electrode 812 in a ring pattern. Bubbles 816 may, for example, be formed and retained at small recessed regions (e.g., about 10-25 µm deep) in the top substrate and/or bottom substrate as described with reference to FIGS. 1 through 3. Bubbles 816 may function as a gasket and provide a barrier to retain a quantity of fluid, such as a fluid droplet 818, at reservoir electrode 812.

Figure 9:
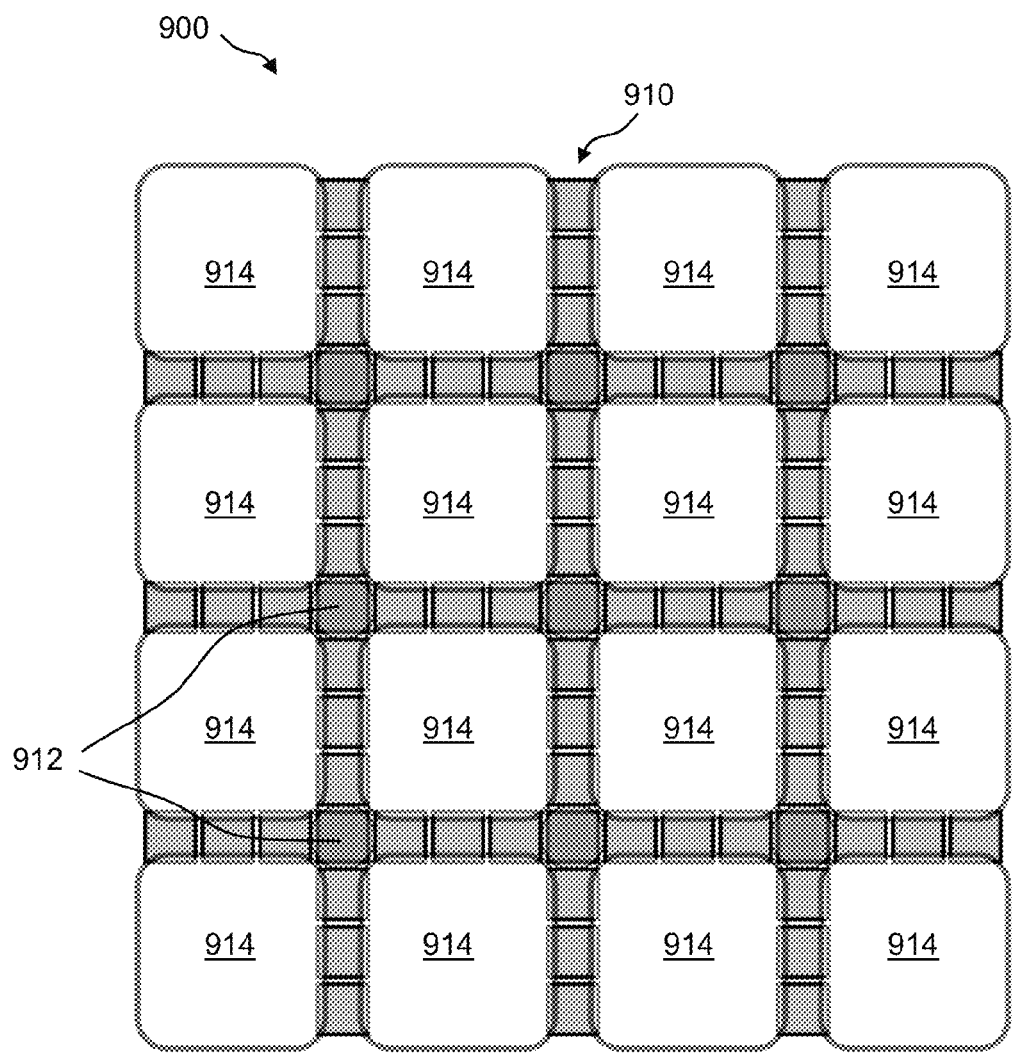
FIG. 9 illustrates a top view of a portion of a droplet actuator and a method of retaining a droplet at a desired position.

FIG. 9 illustrates a top view of a portion of a droplet actuator 900 and a method of retaining a droplet at a desired position. The method of the invention of FIG. 9 uses bubbles (e.g., gaseous bubbles) as a barrier to confine a droplet to a specific location in a droplet actuator in the absence of an electrowetting force. Droplet actuator 900 may include a path or array of droplet operations electrodes 910 formed between two substrates (not shown) that are separated by a gap. Droplet actuator 900 may include one or more droplets 912 that may be transported along droplet operations electrodes 910. One or more bubbles 914 (e.g., gaseous bubbles) may be arranged in close proximity to droplet operations electrodes 910. Bubbles 914 may, for example, be formed in recessed regions in the top substrate and/or bottom substrate as described with reference to FIGS. 1 through 3. Bubbles 914 may be of sufficient size to prevent movement of droplet 912 on droplet operations electrodes 910 in the absence of an electrowetting force. In this example, sixteen bubbles 914 are arranged to confine nine droplets 912 at certain droplet operations electrodes 910 in the absence of an electrowetting force. Any number and pattern of bubbles 914 may be used to provide one or more suitable barriers. In another embodiment, bubbles may be used to provide a barrier to prevent cross-contamination between reaction zones on a droplet actuator. In yet another embodiment, when transporting large volumes of fluids via droplet operations, bubbles may be used to provide a barrier to prevent inappropriate mixing between fluids.

Figure 10:
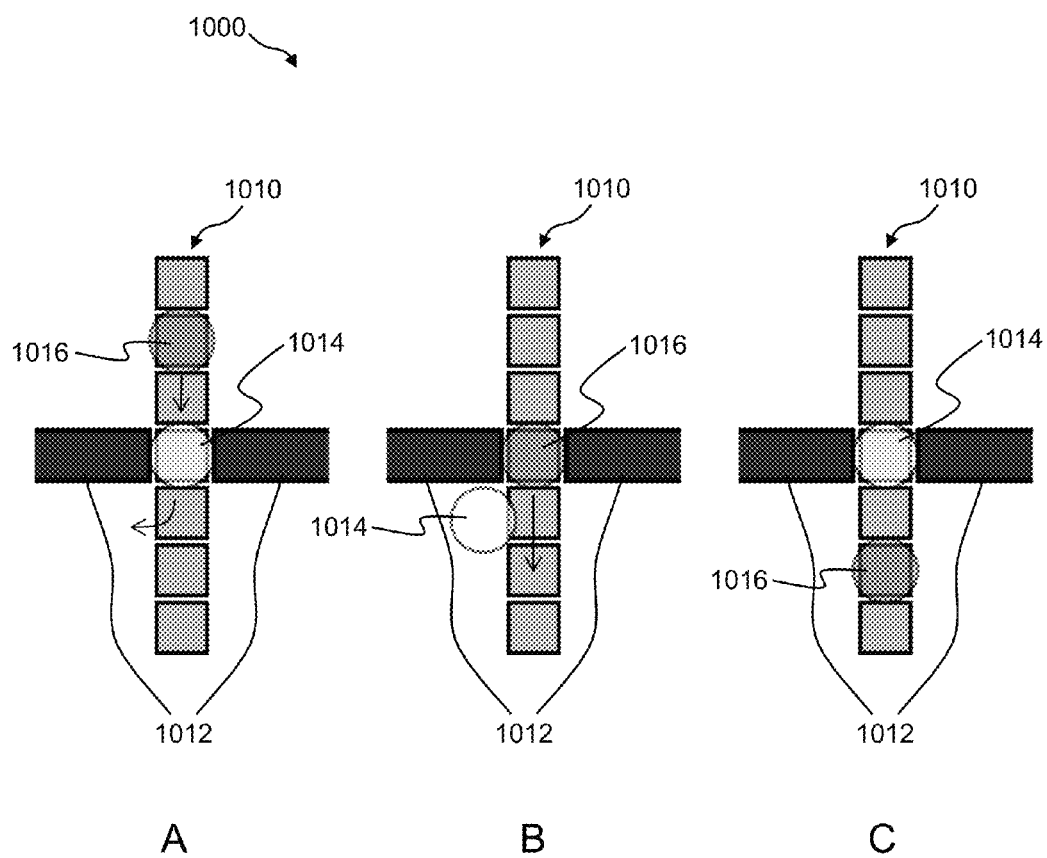
FIGS. 10A through 10C illustrate top views of a portion of a droplet actuator and illustrate a method of using a bubble as a selective gating mechanism.

FIGS. 10A through 10C illustrate top views of a portion of a droplet actuator 1000 and illustrate a method of using a bubble as a selective gating mechanism. The method of the invention of FIGS. 10A through 10C is an example of a bubble-based gating mechanism wherein a bubble is used to selectively allow the transport of certain sized droplets only (e.g., based on volume) during droplet operations. In one example, bubble-based selective gating may be used to allow a sufficiently large volume of liquid (e.g., a slug of fluid) to pass into a certain area of a droplet actuator, while preventing certain smaller volumes of liquid from passing into the area.

Droplet actuator 1000 may be formed of two substrates (not shown) that are separated by a gap. A path or array of droplet operations electrodes 1010 may be associated with one or both substrates of droplet actuator 1000. A recessed region, such as described with reference to FIGS. 1 through 3, is provided at a designated droplet operations electrode 1010. A physical barrier 1012 is provided across the line of droplet operations electrodes 1010 and with an opening at the designated droplet operations electrode 1010. Physical barrier 1012 may be formed, for example, of gasket material. A bubble 1014 (e.g., gaseous bubble) may be formed in the opening of physical barrier 1012 at the designated droplet operations electrode 1010. A droplet 1016 may be transported along droplet operations electrodes 1010 of droplet actuator 1000.

FIG. 10A shows the first step in a process of using a bubble as a selective gating mechanism. In this step, bubble 1014 is positioned in the opening of physical barrier 1012 at the designated droplet operations electrode 1010. Bubble 1014 substantially fills the span of the opening of physical barrier 1012, thereby substantially blocking the designated droplet operations electrode 1010. Further, droplet 1016 is positioned on droplet operations electrode 1010 in proximity to bubble 1014. Droplet 1016 is transported via droplet operations toward bubble 1014.

FIG. 10B shows another step in the process of using a bubble as a selective gating mechanism. In this step, droplet 1016 displaces bubble 1014 from the designated droplet operations electrode 1010 and away from physical barrier 1012. This is because bubble 1014 is of a sufficiently large volume to move bubble 1014. Bubble 1014 may be permanently displaced from the opening of physical barrier 1012. Droplet 1016 is transported through the opening of physical barrier 1012 along droplet operations electrodes 1010. In one example, permanent displacement of a bubble may be used when dispensing a large volume of liquid (e.g., a reagent).

In another example, droplet 1016 is not of a sufficiently large volume to displace bubble 1014 from the opening of physical barrier 1012. In this example, as droplet 1016 is transported toward physical barrier 1012, bubble 1014 is not displaced. Because bubble 1014 is not displaced, the transport of droplet 1016 through the opening of physical barrier 1012 is blocked.

FIG. 10C shows an optional step in the process of using a bubble as a selective gating mechanism. In this step, as droplet 1016 is transported through the opening of physical barrier 1012, displaced bubble 1014 may return to the recessed region in the opening of physical barrier 1012. In an alternative embodiment, bubble 1014 may be forced into a recessed region in step B such that bubble 1014 does not return to the opening.

FIGS. 11A through 11D illustrate top views and side views of a portion of a droplet actuator 1100 and illustrate a method of using a bubble as a reversible gating mechanism. The method of the invention of FIG. 11A through 11D is an example of a reversible gating mechanism. For example, the reversible gating mechanism provides a space (e.g., a pocket) for retaining a bubble. The bubble may be displaced from the pocket during droplet operations and then readily returned to the pocket upon completion of the droplet operations. In one example, a reversible gating mechanism may be used to control the movement of a droplet between different areas of a droplet actuator that are filled with separate filler fluids.

Droplet actuator 1100 includes a bottom substrate 1110 and a top substrate 1112 that are separated by a gap. Droplet actuator 1100 may include a path or array of droplet operations electrodes 1114 (e.g., electrowetting electrodes) that are associated with one or both substrates. A pocket 1116 may be formed at a designated droplet operations electrode 1114. Pocket 1116 may be bounded on one side by a spacer 1118 between bottom substrate 1110 and top substrate 1112. Pocket 1116 may be bounded on the other side by gasket material 1120 that is also between bottom substrate 1110 and top substrate 1112. Gasket material 1120 may be shaped such that the area of pocket 1116 covers the area of the designated droplet operations electrode 1114 and also extends to one side of the designated droplet operations electrode 1114. Further, a beveled notch may be patterned into, for example, top substrate 1112 such that the height of pocket 1116 is greatest near spacer 1118 and least near gasket material 1120. In other words, the gap formed by pocket 1116 is largest near spacer 1118 and smallest near gasket material 1120.

Figure 11:
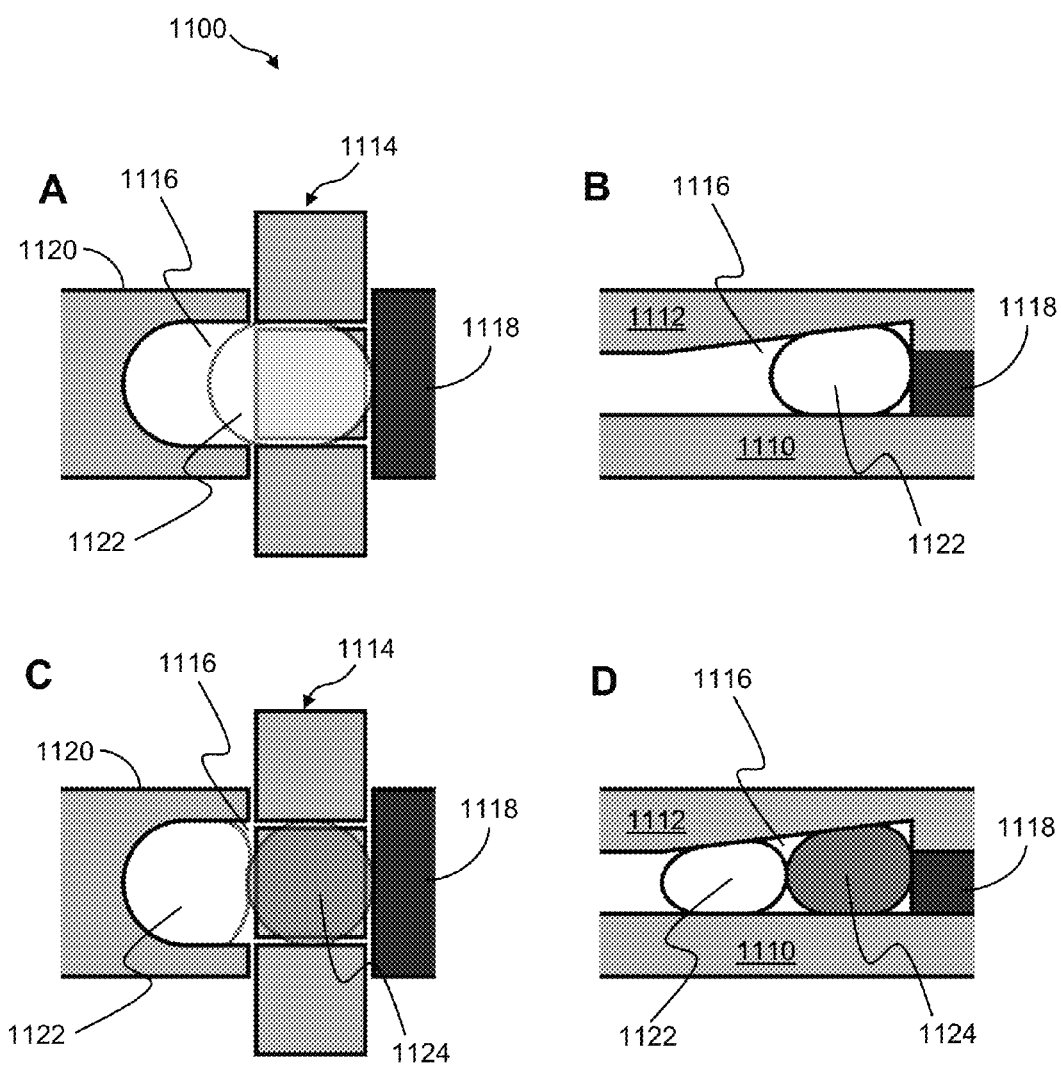
FIGS. 11A through 11D illustrate top views and side views of a portion of a droplet actuator and illustrate a method of using a bubble as a reversible gating mechanism.

In operation, FIGS. 11A and 11B show a bubble 1122 positioned in pocket 1116. Because the gap formed by pocket 1116 is largest near spacer 1118, the pressure is lowest in this region of pocket 1116. Bubble 1122 tends to automatically move to this low pressure region. Therefore, bubble 1122 automatically tends to position itself atop the designated droplet operations electrode 1114. As a result, the line of droplet operations electrodes 1114 is blocked by bubble 1122. Using a switch analogy, with respect to the line of droplet operations electrodes 1114, bubble 1122 is naturally in the "normally blocked" position.

By contrast, FIGS. 11C and 11D show a droplet 124 that is transported via droplet operations to the designated droplet operations electrode 1114 at pocket 1116. The volume of droplet 124 is sufficiently large to displace bubble 1122 to the narrow portion of pocket 1116, which is the high pressure region of pocket 1116. Once droplet 124 is transported out of pocket 1116 via droplet operations, bubble 1122 tends to move from the high pressure region to the low pressure region of pocket 116. As a result, droplet 124 automatically returns to its "normally blocked" position. In this manner, bubble 1122 in pocket 1116 serves to function as a reversible gate (or valve).

In another embodiment, pocket 1116 may be designed to function as a non-reversible gate (or valve). That is, pocket 1116 may be designed such that when bubble 1122 is displaced by droplet 124, it does not return to its original position when droplet 124 is transported out of pocket 1116. In this embodiment, the bubble is initially used to block the line of droplet operations electrodes 1114, but once displaced, it remains displaced.

Figure 12:
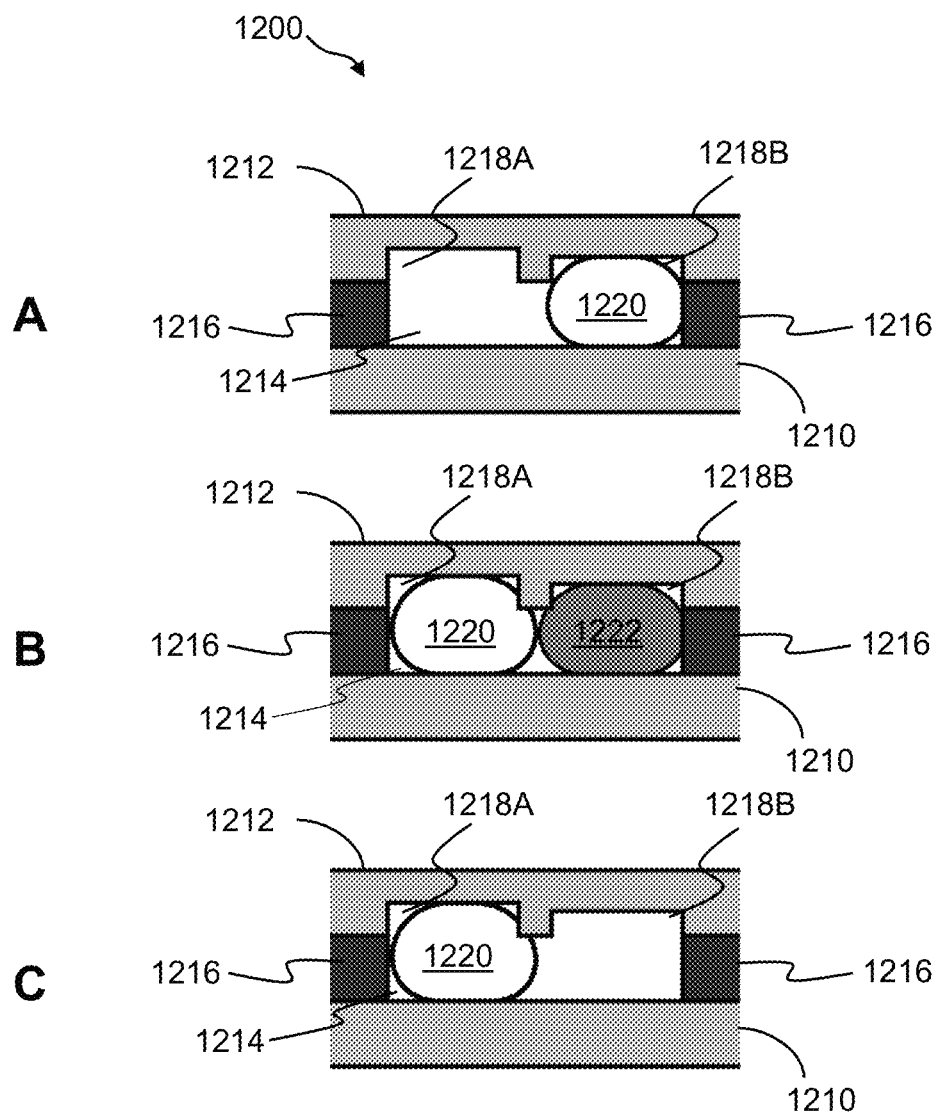
FIGS. 12A through 12C illustrate side views of a portion of a droplet actuator and a method of using a bubble as a non-reversible gating mechanism.

FIGS. 12A through 12C illustrate side views of a portion of a droplet actuator 1200 and a method of using a bubble as a non-reversible gating mechanism. The method of the invention of FIGS. 12A through 12C is an example of a method of a bubble-based gating mechanism wherein a bubble may be displaced laterally during droplet operations.

Droplet actuator 1200 may include a bottom substrate 1210 and a top substrate 1212 that are separated by a gap 1214. One or more spacers 1218 may be between bottom substrate 1210 and top substrate 1212 for determining the height of gap 1214. Top substrate 1212 may include recessed regions 1218A and 1218B. The two recessed regions 1218A and 1218B are of different depth. In one example, recessed region 1218A may be a greater depth than recessed region 1216B. Recessed regions 1218A and 1218B may, for example, be formed in top substrate 1212 by patterning, embossing, and/or etching. Because recessed region 1218A is deeper than recessed region 1218B, the height of gap 1214 is greater at recessed region 1218A than at recessed region 1218B. Consequently, the pressure is lower at recessed region 1218A than at recessed region 1218B.

FIG. 12A shows a first step in a process of permanently displacing a bubble in a bubble-based gating mechanism. In this step, a bubble 1220 is initially positioned at recessed region 1218B, which has higher pressure than recessed region 1218A.

FIG. 12B shows another step in the process of permanently displacing a bubble in a bubble-based gating mechanism. In this step, a droplet 1222 is transported on droplet operations electrodes (not shown) via electrowetting to recessed region 1216B. As droplet 1222 is transported into recessed region 1216B, bubble 1220 is displaced laterally into recessed region 1216A, which has lower pressure than recessed region 1218A.

FIG. 12C shows another step in the process of permanently displacing a bubble in a bubble-based gating mechanism. In this step, droplet 1222 is transported away from recessed region 1216B. Because recessed region 1216A is of lower pressure than recessed region 1216B, bubble 1220 tends to be retained at recessed region 1216A.

Figure 13:
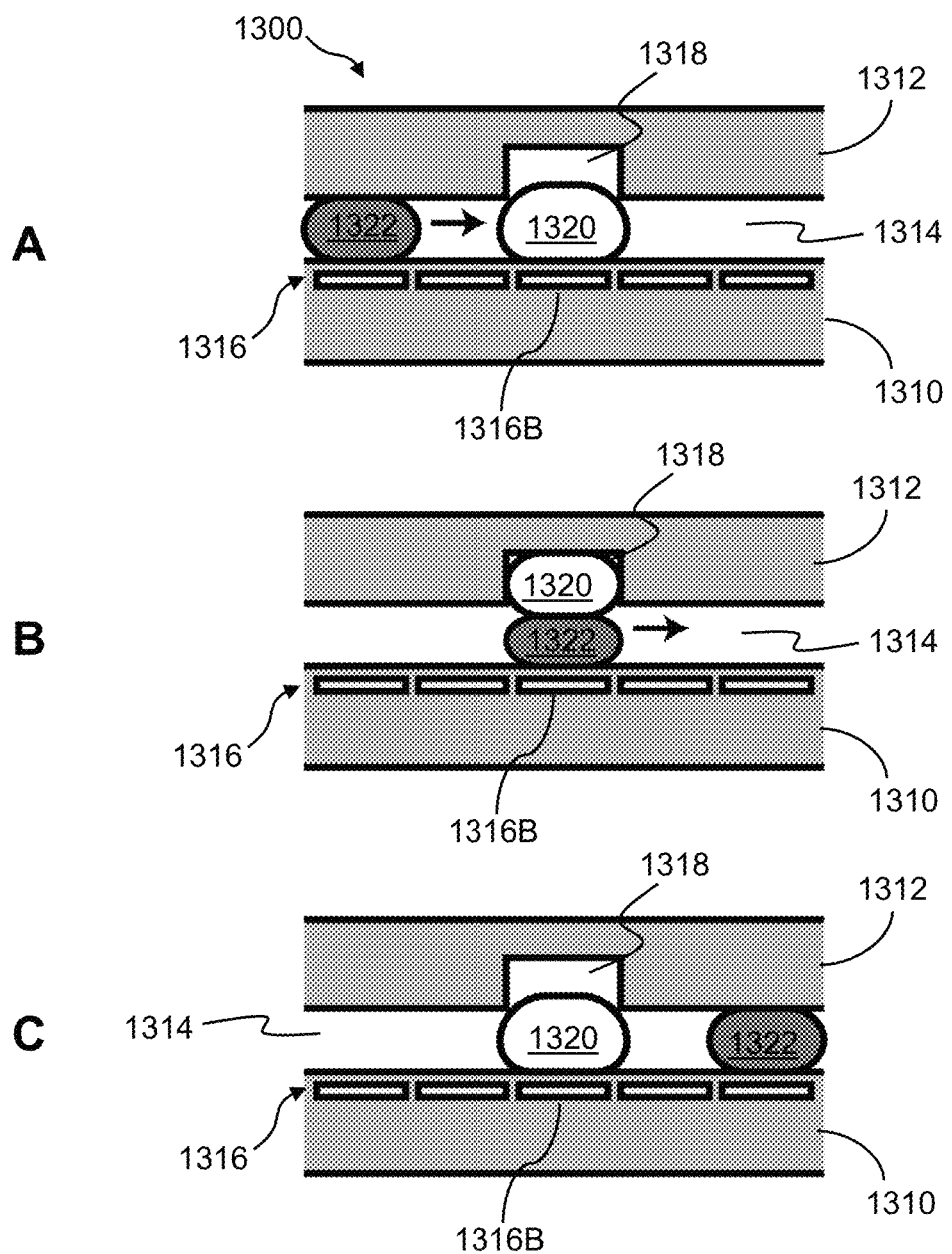
FIGS. 13A through 13C illustrate side views of a portion of a droplet actuator and illustrate another method of using a bubble as a reversible gating mechanism.

FIGS. 13A through 13C illustrate side views of a portion of a droplet actuator 1300 and illustrate another method of using a bubble as a reversible gating mechanism. The method of the invention of FIG. 13A through 13C is an example of a reversible gating mechanism wherein a recessed region is provided within a top substrate such that a bubble is readily returned to position after vertical displacement during droplet operations.

Droplet actuator 1300 may include a bottom substrate 1310 and a top substrate 1312 that are separated by a gap 1314. Bottom substrate 1310 may include a path or array of droplet operations electrodes 1316 (e.g., electrowetting electrodes). Top substrate 1312 may include a recessed region 1318. Recessed region 1318 may, for example, be formed in top substrate 1312 by patterning, embossing, and/or etching. Recessed region 1318 may be substantially aligned with a designated droplet operations electrode 1316B. Recessed region 1318 may be of sufficient depth to accommodate a bubble 1320. In another embodiment, a recessed region may be provided in bottom substrate 1310.

FIG. 13A shows a first step in a process of using a bubble as a gating mechanism. In this step, bubble 1320 is positioned in gap 1314 and atop the droplet operations electrode 1316B at recessed region 1318. Via droplet operations, a droplet 1322 is transported along droplet operations electrodes 1316 toward bubble 1320.

FIG. 13B shows another step in the process of using a bubble as a gating mechanism. In this step, droplet 1322 is transported to the droplet operations electrode 1316B at recessed region 1318. In doing so, bubble 1320 is displaced into recessed region 1318 and droplet 1322 is sandwiched between bubble 1320 and the droplet operations electrode 1316B.

FIG. 13C shows another step in the process of using a bubble as a gating mechanism. In this step, droplet 1322 is transported away from the droplet operations electrode 1316B at recessed region 1318. As droplet 1322 is transported away from droplet operations electrode 1316B, bubble 1320 leaves recessed region 1318 and returns to its original position in gap 1314 and atop the droplet operations electrode 1316B.

FIGS. 14A through 14C illustrate side views of a portion of a droplet actuator 1400 and another method of using a bubble as a non-reversible gating mechanism. The method of the invention of FIGS. 14A through 14C is an example of a method of a gating mechanism wherein a bubble is displaced vertically during droplet operations.

Droplet actuator 1400 may include a bottom substrate 1410 and a top substrate 1412 that are separated by a gap 1414. Gap 1414 may include a filler fluid 1416, such as an oil-based filler fluid. Bottom substrate 1410 may include a path or array of droplet operations electrodes 1418 (e.g., electrowetting electrodes). Top substrate 1412 may include a recessed region 1420. Recessed region 1420 may, for example, be formed in top substrate 1412 by patterning, embossing, and/or etching. Recessed region 1420 may be of sufficient depth to accommodate and retain a bubble 1422.

FIG. 14A shows a first step in a process of displacing a bubble in a gating mechanism during droplet operations. In this step, bubble 1422 is positioned along droplet operations electrode 1418 in proximity to recessed region 1420. A droplet 1424 is positioned in proximity of bubble 1422 such that bubble 1422 is between droplet 1424 and recessed region 1420. Via droplet operations, droplet 1424 is transported along droplet operations electrodes 1418 (toward bubble 1422).

FIG. 14B shows another step in the process of displacing a bubble in a gating mechanism during droplet operations. In this step, droplet 1424 comes into contact with bubble 1422 and pushes it toward recessed region 1420. When bubble 1422 reaches recessed region 1420, it is displaced from droplet operations electrodes 1418 into recessed region 1420. For example, bubble 1422 floats to the top of oil-based filler fluid in recessed region 1420.

FIG. 14C shows another step in the process of displacing a bubble in a gating mechanism during droplet operations. In this step, droplet 1424 continues to be transported along droplet operations electrodes 1418 and past recessed region 1420, leaving bubble 1422 behind in recessed region 1420.

Figure 14:
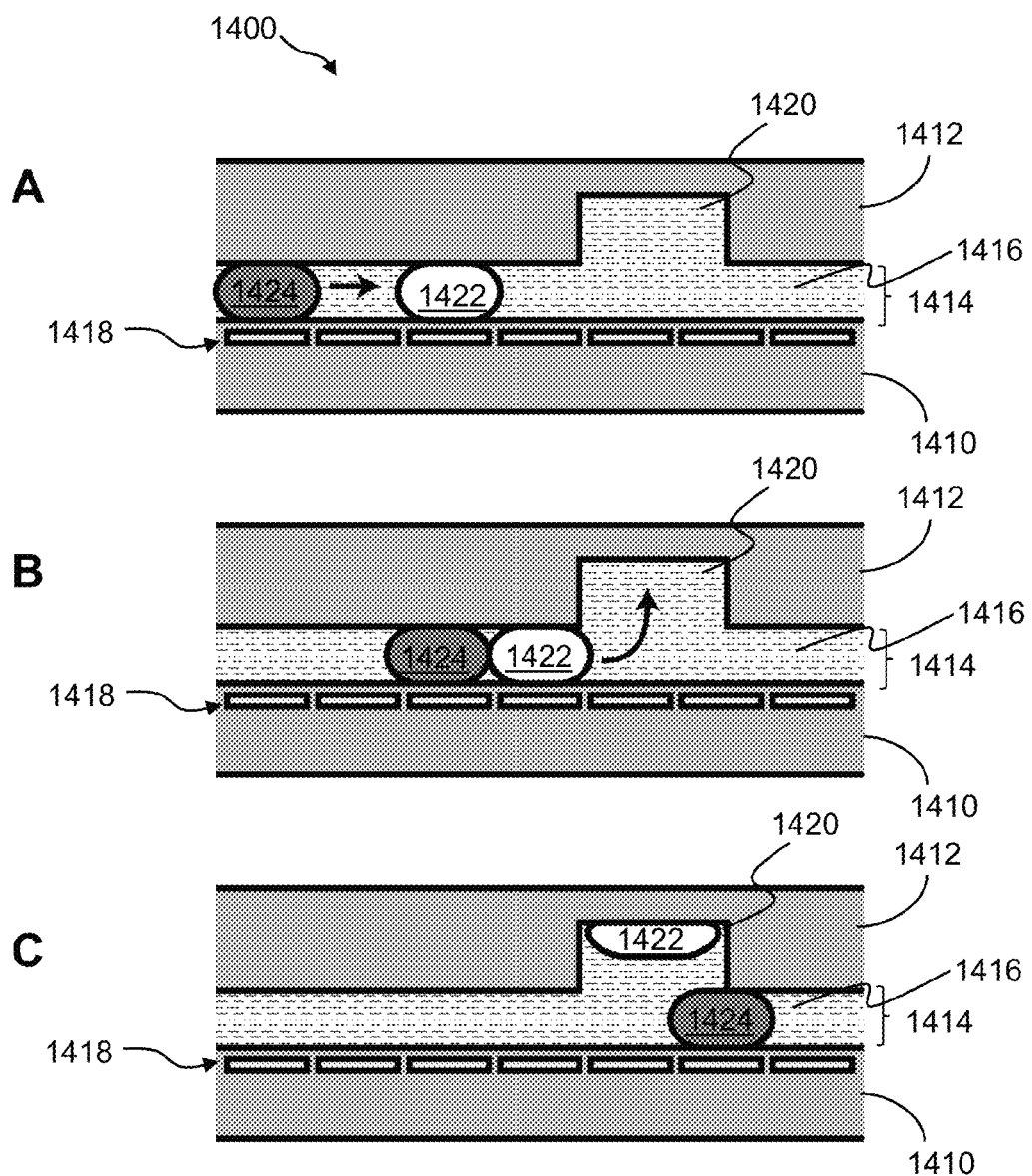
FIGS. 14A through 14C illustrate side views of a portion of a droplet actuator and another method of using a bubble as a non-reversible gating mechanism.

In another embodiment, the method of the invention of FIG. 14 may be used to sequester a quantity of air in a droplet actuator. For example, air trapped in recessed regions may be used in applications of cell cultures on a droplet actuator.

FIGS. 15A through 15D illustrate top views of a portion of a droplet actuator 1500 and show a method of monitoring the flow of fluid from a reservoir into a droplet actuator. The method of the invention of FIGS. 15A through 15D is an example of a feedback mechanism wherein the difference in capacitance between a fluid and a bubble (e.g., gaseous bubble) is used to monitor dispensing of a quantity of fluid. In one example, the feedback mechanism may be used to monitor availability of a reagent from a reservoir prior to using the droplet actuator for a molecular assay.

Droplet actuator 1500 may be formed of two substrates (not shown) that are separated by a gap. Droplet actuator 1500 may include a fluid reservoir 1505. A reservoir electrode 1510 is associated with fluid reservoir 1505. Reservoir electrode 1510 feeds, for example, a line of droplet operations electrodes 1512 (e.g., electrowetting electrodes). Fluid reservoir 1505 may be bounded by a barrier 1514, which may be formed of, for example, gasket material. An opening 1516 in a top substrate (not shown) may be provided in proximity to reservoir electrode 1510. Opening 1516 provides a fluid path for dispensing a quantity of fluid onto reservoir electrode 1510. The process of using a bubble to monitor the dispensing of a quantity of fluid from a reservoir may include, but is not limited to, the following steps.

Figure 15:
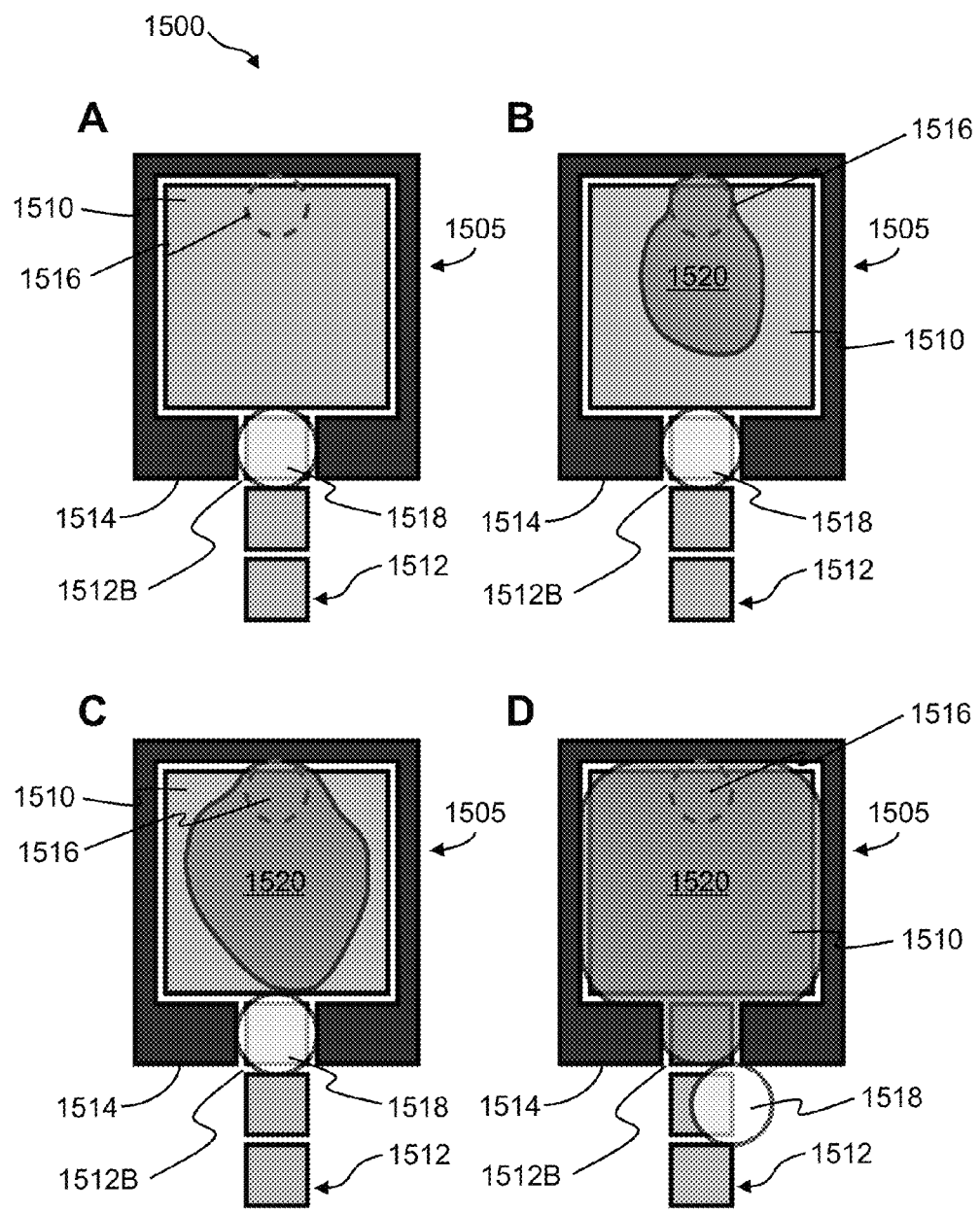
FIGS. 15A through 15D illustrate top views of a portion of a droplet actuator and show a method of monitoring the flow of fluid from a reservoir into a droplet actuator.

FIG. 15A shows a first step in a process of using a bubble to monitor the dispensing of a quantity of fluid from a reservoir. In this step, a bubble 1518 may be positioned on a certain droplet operations electrode 1512 (e.g., droplet operations electrode 1512B) adjacent to reservoir electrode 1510. The capacitance at droplet operations electrode 1512B is measured with bubble 1518 positioned thereon. This capacitance value may be stored and is hereafter referred to as the "reference value."

FIG. 15B shows another step in the process of using a bubble to monitor the dispensing of a quantity of fluid from a reservoir. In this step, a quantity of fluid 1520 (e.g., wash buffer) is loaded onto reservoir electrode 1510 through opening 1516. As fluid 1520 fills fluid reservoir 1505, the capacitance at droplet operations electrode 1512B is measured in order to determine whether the capacitance has changed from the reference value.

FIG. 15C shows another step in the process of using a bubble to monitor the dispensing of a quantity of fluid from a reservoir. In this step, fluid 1520 is further distributed across the area of reservoir electrode 1510 and in proximity to droplet operations electrode 1512B. As fluid 1520 further fills fluid reservoir 1505, the capacitance at droplet operations electrode 1512B is measured in order to determine whether the capacitance has changed from the reference value.

FIG. 15D shows another step in the process of using a bubble to monitor the dispensing of a quantity of fluid from a reservoir. In this step, fluid 1520 has substantially filled reservoir fluid reservoir 1505 and fluid 1520 displaces bubble 1518 at droplet operations electrode 1512B. Yet again, the capacitance at droplet operations electrode 1512B is measured in order to determine whether the capacitance has changed from the reference value. In this step, a change in capacitance may be detected because fluid 1520 is now present atop droplet operations electrode 1512B, instead of bubble 1518. This change in capacitance with respect to the reference value may be used to indicate that liquid has flowed out of fluid reservoir 1505 and onto droplet operations electrodes 1512.

In one embodiment, once displaced, bubble 1518 may return to droplet operations electrode 1512B in the absence of fluid 1520. In another embodiment, a recessed region, such as described in FIGS. 1 through 3 and/or in FIG. 14, may be provided along side of droplet operations electrode 1512B. Once displaced, bubble 1518 may be retained in the recessed region and not returned to droplet operations electrode 1512B in the absence of fluid 1520. In this embodiment, a capacitance measurement may be taken at the recessed region and/or at droplet operations electrode 1512B in order to determine whether fluid 1520 has flowed out of fluid reservoir 1505 and onto droplet operations electrodes 1512.

Figure 16:
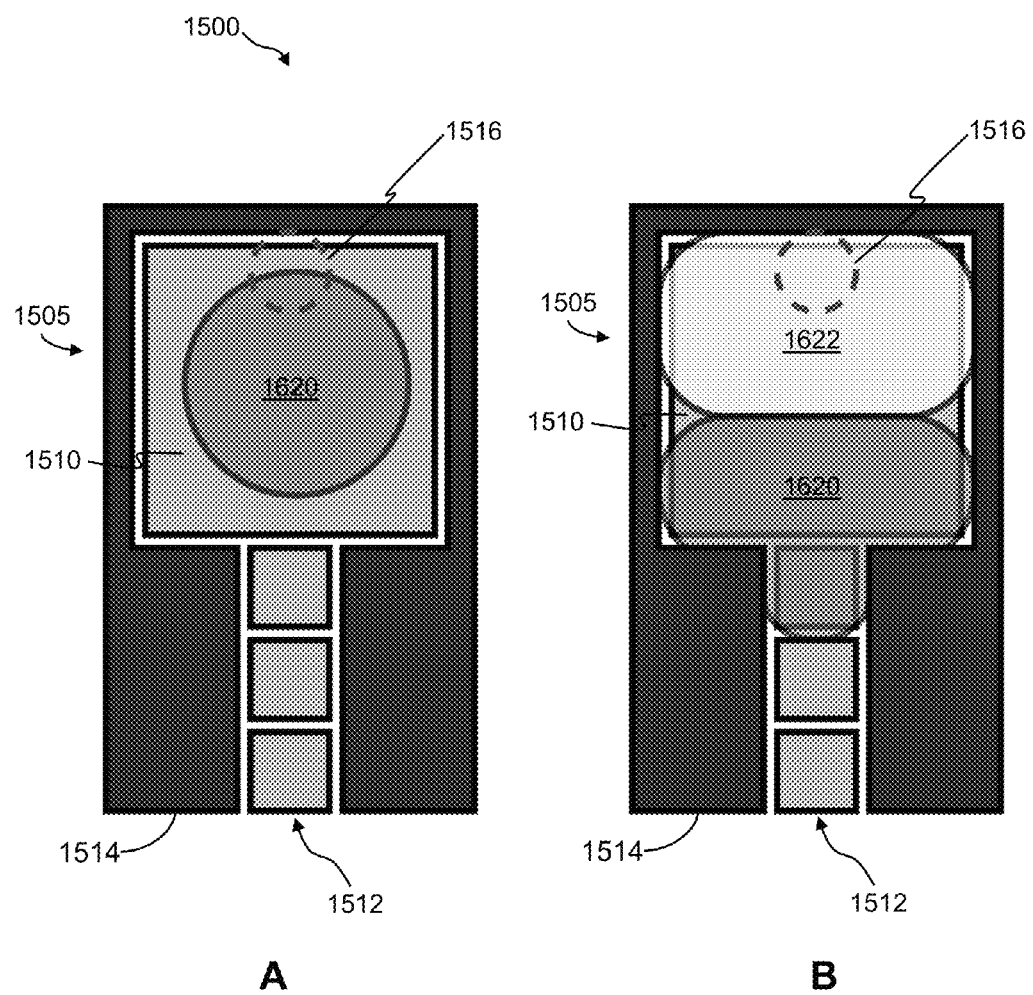
FIGS. 16A and 16B illustrate top views of a portion of the droplet actuator of FIGS. 15A through 15D and show a method of facilitating the dispensing of a small quantity of fluid from a reservoir.

FIGS. 16A and 16B illustrate top views of a portion of the droplet actuator 1500 of FIGS. 15A through 15D and show a method of facilitating the dispensing of a small quantity of fluid from a reservoir. The method of the invention of FIGS. 16A and 16B is an example of a pressure-assisted dispensing that uses a bubble to facilitate dispensing of a fluid from a reservoir.

FIG. 16A shows a first step in a process of using a bubble to facilitate dispensing of a small quantity of fluid from a reservoir. In this step, a small volume of fluid 1620 is loaded (e.g., by pipetting) through opening 1518 of fluid reservoir 1505 and onto reservoir electrode 1510. Because of its small volume, fluid 1620 is not in sufficient proximity to droplet operations electrodes 1512 to allow effective dispensing onto droplet operations electrodes 1512.

FIG. 16B shows another step in a process of using a bubble to facilitate dispensing of a small quantity of fluid from a reservoir. In this step, a bubble 1622 (e.g., gaseous bubble) is forced (e.g., by pipetting) onto reservoir electrode 1510 through opening 1518 of fluid reservoir 1505. In this example, bubble 1622 may be an externally generated bubble. Bubble 1622 is of sufficient size to displace fluid 1620 into sufficient proximity to droplet operations electrodes 1512. Droplet operations electrodes 1512 are activated (i.e., turned ON) and, thus, droplets (not shown) may be effectively dispensed from fluid 1620.

In another embodiment, a bubble(s) for pressure-assisted dispensing may be generated internally. For example, a bubble (e.g., vapor bubble) may be generated on a droplet actuator by heating or electrolysis. The size of the bubble may be dynamically controlled by heating and cooling.

In any of the embodiments described herein, the contents of a droplet actuator may be provided under greater-than-atmospheric pressure in order to provided bubbles of concentrated gas on the droplet actuator. In other embodiments, the contents of a droplet actuator may be provided under atmospheric pressure or less-than-atmospheric pressure.

8 Concluding Remarks

The foregoing detailed description of embodiments refers to the accompanying drawings, which illustrate specific embodiments of the invention. Other embodiments having different structures and operations do not depart from the scope of the present invention. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

We claim:

1. A method of forming a bubble in a droplet actuator, the method comprising:
  (a) providing a droplet actuator comprising:
    (i) one or more substrates configured to form a droplet operations gap, the one or more substrates comprising electrodes arranged for conducting droplet operations in the droplet operations gap; and
    (ii) a physical or chemical feature provided at a predetermined locus within or exposed to the droplet operations gap and configured to retain a bubble in position within the droplet operations gap; and
  (b) dispensing an oil filler fluid, which fluid is sufficiently immiscible with a droplet phase to render the droplet phase subject to electrode-mediated droplet operations, into the droplet operations gap at a rate and volume sufficient to fill the fluid reservoir and to form a gaseous bubble at the physical or chemical feature, wherein the gaseous bubble is at least partially surrounded by the oil filler fluid.

2. The method of claim 1 wherein the droplet actuator further comprises more than one of the physical or chemical features.

3. The method of claim 2 wherein the droplet actuator further comprises an array of the chemical or physical features and an array of bubbles formed in the droplet operations gap and surrounded by an oil filler fluid.

4. The method of claim 3 wherein the droplet actuator further comprises an array of dried reagent, each dried reagent situated within a gaseous bubble in the array of bubbles.

5. The method of claim 1 wherein the physical feature comprises a recessed region of a surface of the one or more substrates facing the droplet operations gap.

6. The method of claim 1 wherein the physical feature comprises recessed regions of opposing surfaces of the one or more substrates facing the droplet operations gap.

7. The method of claim 1 wherein the physical feature comprises a chemically treated region of a surface of the one or more substrates facing the droplet operations gap.

8. The method of claim 1 wherein the physical feature comprises a hydrophilic or lipophobic region of a surface of the one or more substrates facing the droplet operations gap.

9. The method of claim 1 wherein the bubble spans the gap between opposing surfaces of the one or more substrates facing the droplet operations gap.

10. The method of claim 1 wherein the bubble comprises a gaseous bubble substantially surrounded by the oil filler fluid within the droplet operations gap.

11. The method of claim 1 wherein the oil filler fluid comprises low viscosity oil.

12. The method of claim 1 wherein the oil filler fluid comprises low viscosity oil doped with a surfactant.

13. The method of claim 1 wherein:
(a) the one or more substrates comprise a top substrate and a bottom substrate; and
(b) the bottom substrate is separated from the top substrate by a gap defined by a spacer to form the droplet operations gap.

14. The method of claim 13 wherein the physical feature comprises a recessed region of a surface of the one or more substrates facing the droplet operations gap.

15. The method of claim 14 wherein the recessed region is on the top substrate facing the bottom substrate, and the bottom substrate further comprises a recessed region opposite to the recessed region of the top substrate.

16. The method of claim 15 wherein the top substrate recessed region and bottom substrate recessed region are of sufficient depth to form a bubble as filler fluid is flowed into the gap, and for retaining a bubble in position in the gap.

17. The method of claim 14 wherein the recessed region is formed by a technique comprising patterning, embossing and/or etching.

18. The method of claim 14 wherein the recessed region is provided only in the top substrate.

19. The method of claim 14 wherein the recessed region is provided only in the bottom substrate.

20. The method of claim 1 wherein the droplet actuator further comprises a fluid reservoir formed in the droplet operations gap and comprising the bubble, the fluid reservoir comprising fluid barriers which at least partially surround the bubble.

21. The method of claim 1 wherein the droplet actuator further comprises a path of electrodes arranged for transporting a droplet situated in the droplet operations gap into the reservoir.

22. The method of claim 1 wherein the bubble is arranged to restrain movement of a droplet in the filler fluid.

23. The method of claim 1 wherein the droplet actuator comprises a fluid path arranged for flowing fluid from a source which is external to the droplet operations gap into the bubble.

24. The method of claim 1 wherein the droplet actuator further comprises a dried reagent situated within the gaseous bubble.

25. The method of claim 1 wherein the bubble comprises a preselected gas composition.

26. The method of claim 1 wherein the bubble comprises a preselected gas composition that is not air.

27. The method of claim 1 wherein the bubble consists substantially of a single gas.

28. The method of claim 1 wherein the bubble is formed under pressure.

29. The method of claim 1 wherein the droplet actuator further comprises a temperature control element arranged to control temperature of the bubble.

30. The method of claim 1 wherein the droplet actuator further comprises one or more physical barriers arranged to restrain movement of the bubble.

31. A method of providing a droplet actuator comprising a bubble in a droplet operations gap thereof, the method comprising:
(a) forming a gaseous bubble in a droplet operations gap of a droplet actuator, comprising electrodes arranged for conducting droplet operations in the droplet operations gap; and a physical or chemical feature provided at a predetermined locus within or exposed to the droplet operations gap and configured to retain a bubble in position within the droplet operations gap;
wherein the bubble is:
(i) at least partially surrounded by an oil filler fluid, which fluid is sufficiently immiscible with a droplet phase to render the droplet phase subject to electrode-mediated droplet operations; and
(ii) optionally, partially surrounded by one or more droplet actuator surfaces; and
(b) forming an aqueous droplet in the filler fluid, wherein the droplet is substantially immiscible with and surrounded by the filler fluid.

32. The method of claim 31 further comprising transporting, by droplet operations mediated by the electrodes, the droplet from the oil filler fluid into the bubble.

33. The method of claim 32 further comprising subjecting the droplet to one or more droplet operations within the bubble.

34. The method of claim 32 further comprising evaporating the droplet within the bubble.

35. The method of claim 32 further comprising evaporating a portion of the droplet to concentrate one or more components in the droplet.

36. The method of claim 31 further comprising providing a dried reagent in the bubble.

37. The method of claim 36 further comprising transporting a droplet from the filler fluid into the bubble to reconstitute the dried reagent.

38. The method of claim 37 wherein transporting the droplet from the filler fluid into the bubble is mediated by the electrodes.

39. The method of claim 31 wherein forming a gaseous bubble in a droplet operations gap of a droplet actuator comprises flowing the oil filler fluid into the droplet operations gap at a rate and volume sufficient to cause formation of a bubble in the droplet operations gap at the predetermined locus.

40. The method of claim 31 wherein the bubble comprises a preselected gas composition.

41. The method of claim 31 wherein the bubble consists substantially of a single gas.

42. The method of claim 31 wherein the bubble is formed under pressure.

43. The method of claim 31 wherein the droplet actuator comprises one or more physical barriers in the reservoir for supporting and retaining the bubble in the reservoir.

44. The method of claim 31 further comprising flowing the bubble out of the droplet operations gap.

45. The method of claim 31 further comprising flowing the bubble into a different region of the droplet operations gap.

46. The method of claim 31 further comprising using the bubble to prevent movement of the droplet.

* * * * *